(12) United States Patent
Nordvall et al.

(10) Patent No.: US 8,088,780 B2
(45) Date of Patent: Jan. 3, 2012

(54) 5,7-DISUBSTITUTED THIAZOLO[4,5-D]PYRIMIDINES FOR THE SELECTIVE INHIBITION OF CHEMOKINE RECEPTORS

(75) Inventors: Gunnar Nordvall, Sodertalje (SE); Colin Ray, Sodertalje (SE); Tobias Rein, Sodertalje (SE); Daniel Sohn, Sodertalje (SE)

(73) Assignee: AstraZeneca AB, Sodertalje (SE)

( * ) Notice: Subject to any disclaimer, the term of this patent is extended or adjusted under 35 U.S.C. 154(b) by 365 days.

(21) Appl. No.: 11/910,781

(22) PCT Filed: Apr. 3, 2006

(86) PCT No.: PCT/SE2006/000398
§ 371 (c)(1),
(2), (4) Date: Oct. 5, 2007

(87) PCT Pub. No.: WO2006/107257
PCT Pub. Date: Oct. 12, 2006

(65) Prior Publication Data
US 2009/0124637 A1 May 14, 2009

(30) Foreign Application Priority Data
Apr. 6, 2005 (SE) .................................... 0500768

(51) Int. Cl.
C07D 487/04 (2006.01)
A61K 31/519 (2006.01)
A61P 11/06 (2006.01)
A61P 9/10 (2006.01)
A61P 37/06 (2006.01)

(52) U.S. Cl. .................................... 514/260.1; 544/255
(58) Field of Classification Search .................. 544/255; 514/260.1
See application file for complete search history.

(56) References Cited

U.S. PATENT DOCUMENTS

| | | | |
|---|---|---|---|
| 2,772,164 A | 11/1956 | Allen et al. | |
| 4,639,433 A | 1/1987 | Hunt et al. | |
| 4,643,987 A | 2/1987 | Nagarajan et al. | |
| 4,698,327 A | 10/1987 | Nagarajan et al. | |
| 5,202,328 A | 4/1993 | De Laszlo et al. | |
| 5,591,714 A | 1/1997 | Nagarajan et al. | |
| 5,840,684 A | 11/1998 | Cooper et al. | |
| 6,107,294 A | 8/2000 | Beck | |
| 6,790,850 B1 * | 9/2004 | Willis et al. | 514/260.1 |
| 6,806,273 B1 | 10/2004 | Austin et al. | |
| 7,067,657 B2 | 6/2006 | Hanson et al. | |
| 2003/0107189 A1 | 6/2003 | Bonnert et al. | |
| 2007/0142386 A1 * | 6/2007 | Nordvall et al. | 514/251 |

FOREIGN PATENT DOCUMENTS

| | | |
|---|---|---|
| EP | 0435503 A1 | 7/1991 |
| WO | WO-9956760 A1 | 11/1999 |
| WO | WO-0009511 A1 | 2/2000 |
| WO | WO-0125242 A1 | 4/2001 |
| WO | WO-0158906 A1 | 8/2001 |
| WO | WO-0158907 A1 | 8/2001 |
| WO | WO-0162758 | 8/2001 |
| WO | WO-02076990 A1 | 10/2002 |
| WO | WO-02083693 A1 | 10/2002 |
| WO | WO-2004026835 A1 | 4/2004 |
| WO | WO-2004026880 A1 | 4/2004 |
| WO | WO-2005033115 A1 | 4/2005 |
| WO | WO-2006107258 A1 | 10/2006 |

OTHER PUBLICATIONS

"Decreased Atherosclerotic Lesion Formation in CX3CR1/Apolipoprotein E Double Knockout Mice," Circulation, 2003, pp. 1009-1016.
Abstract of "The CX3C chemokine fractalkine in allergic asthma and rhinits," J. Allergy Clin. Immunol., Dec. 2003; 112(6), pp. 1139-1146.
Abstract of "A closer look at chemokines and their role in asthmatic responses," European Journal of Pharmacology, vol. 533, Issues 1-3, 2006.
Abstract of "Decreased atherosclerosis in CX3CR1-/-mice reveals a role for fractalkine in atherogenesis," J. Clin Invest. Feb. 2003 111(3): 333-40.
Abstract of "Fractalkine is an epithelial and endothelial cell-derived chemoattractant for intraepithelial lymphocytes in the small intestinal mucosa," J. Immunol. Mar. 2000 15:164(6).
"The Chemokine Fractalkine Inhibits Fas-Mediated Cell Death of Brain Microglia," *The Journal of Immunology*, 2000, 165, pp. 1-16.
Abstract of "Role of Fractalkine (CX3CL1) in Regulating Neuron-Microglia Interactions: Development of Viral-Based CX3CR1 Antagonists," Current Alzheimer Research, vol. 2, No. 2, Apr. 2005.
"Chemokines and Chemokine Receptors in Autoimmune Encephalomyelitis as a Model for Central Nervous System Inflammatory Disease Regulation," Frontiers in Bioscience, 9, May 1, 2004, pp. 1500-1505.
Chemokine and Chemokine Receptor Expression in the Central Nervous System, Journal of NeuroVirology (1999) 5, pp. 13-26.
Abstract of "CX3CR1-Fractalkine Expression Regulates Cellular Mechanisms Involved in Adhesion, Migration, and Survival of Human Prostate Cancer Cells," Cancer Research 64, pp. 4693-4698, Jul. 15, 2004.
"Chemokines and Chemokine Receptors: Their Manifold Roles in Homeostasis and Disease," Cellular and Molecular Immunology, vol. 1, No. 2, 2004, pp. 95-104.
Abstract of "A new class of membrane-bound chemokine with a CX3C motif," Nature, 385, Feb. 13, 1997.

(Continued)

Primary Examiner — Susanna Moore

(57) ABSTRACT

There are disclosed novel 5,7-disubstituted [1,3]thiazolo[4,5-d]pyrimidin-2(3H)-one derivatives of formula (I) wherein $R^1$, $R^2$, $R^3$, $R^4$ and $R^5$ are as defined in the specification, and pharmaceutically acceptable salts thereof, together with processes for their preparation, pharmaceutical compositions comprising them and their use in therapy. The compounds of formula (I) are $CX_3CR1$ receptor antagonists and are thereby particularly useful in the treatment or prophylaxis of neurodegenerative disorders, demyelinating disease, cardio- and cerebrovascular atherosclerotic disorders, peripheral artery disease, rheumatoid arthritis, pulmonary diseases such as COPD, asthma or pain.

10 Claims, No Drawings

OTHER PUBLICATIONS

Baker et al., "Synthesis of Derivatives of Thiazolo . . . ," J. Chem. Soc., pp. 2478-2484 (1970).

Balabanian et al., "CX3C Chemokine Fractalkine in Pulmonary Arterial Hypertension," Am.J. Respir. Cnt. Care Med. 165, pp. 1419-1425 (2002).

Chapman et al., "Fractalkine Cleavage from Neuronal Membranes Represents an Acute Event in the Inflammatory Response to Excitotoxic Brain Damage," J. Neuroscience 20, pp. 1-5 (2000).

Cooper et al., J. Antibiotics, 49:6, pp. 575-581 (1996).

Maggiolo et al., "Studies on Condensed Pyrimidine Systems . . . ," J. Amer. Chem. Soc. vol. 73, pp. 4226-4228 (1951).

Moatti et al., "Polymorphism in the Fractalkine Receptor CX3CRI as a Genetic Risk Factor for Coronary Artery Disease," Blood, 97, pp. 1925-1928 (2001).

Nagarajan et al., "Synthesis and Antibacterial activity of N-acyl Vancomycins," J. Antibiotics, 41:10, pp. 1430-1438 (1988).

Pfleiderer et al., "Pteridine, XXVII 1) Synthese und Struktur von 7-Hydroxy-isopterinen," Chemische Berichte, vol. 96, No. 11, pp. 2964-2976, Table 2, Compound 5 (1963).

Ruth et al., "Fractalkine, a Novel Chemokine in Rheumatoid Arthritis and Rat Adjuvant-Induced Arthritis," Arthritis Rheum. 44, pp. 1568-1581 (2001).

Sariano et al., "Mice Deficient in Fractalkine are less Susceptible to Cerebral IschemiaReperfusion Injury," J. Neuroinununol, 125, pp. 59-65 (2002).

STN International, file CAPLUS accession No. 1990-235252, Ahluwalia et al., "One step Synthesis of thiazolo . . . " (1989).

STN International, file CAPLUS accession No. 1996-243961, Gewald et al., "New Synthesis of substituted . . . " (1996).

STN International, file Caplus accession No. 1990-158124, Pawar et al., "Studies on the Vilsmeier-Haak Reaction . . . " (1989).

STN International, file CA, Chem Abstract, vol. 60, Pfleiderer et al., "Original Ref. No. 60:5486h, 5487a-h." "Synthesis and Structure of 7-Hydroxysiopterines," Abstract No. 30913, 1963.

Takahashi et al., "Studies on Pyrimidine Derivatives . . . , " Chem. Pharm. Bull, vol. 6, pp. 334-338 (1958).

Tarozzo et al., "Expression of Fractalkine and its Receptor, CX3CR1, in Response to Ischaemia-Reperfusion Brain injury in the Rat," Eur. J. Neuroscience 15, pp. 1663-1668 (2002).

Twining et al., "Sinal fractalkine Induces Allodynia & Hyperalgesia," Society for Neuroscience 27, 732, Abstract No. 279, 12 (2001).

Umehara et al., "Arterioscler Thromb vase Biol.," 2004 Jan; 24(1), pp. 34-40, Epub. Sep. 11 2003.

Umehara et al., "Fractalkine and Vascular Injury," Trends Immunol. 22, pp. 602-607 (2001).

Verge et al., "Mapping Fractalkine and its Receptor (Cx3CRI) in a Rat Model of Inflammatoryneuropathu," IASP Abstract No. 393 p. 27 (2002).

Volin et al., "Fractalkine: A Novel Angiogenic Chemokine in Rheumatoid Arthritis," Am. J. Pathology, 156, pp. 1521-1530 (2001).

Watkins et al., "Spinal Fractalkine: KeyPlayer in Exaggerated Pain States," IASP Abstract No. 390, p. 24 (2002).

Zujovic et al., "Fractalkine Modulates TNF-alpha Secretion and Neurotoxicity Induced by Microglial Activation," GLIA 29, pp. 305-315 (2000).

* cited by examiner

5,7-DISUBSTITUTED THIAZOLO[4,5-D]PYRIMIDINES FOR THE SELECTIVE INHIBITION OF CHEMOKINE RECEPTORS

CROSS-REFERENCE TO RELATED APPLICATIONS

This application is a US National Stage under 35 U.S.C. §371 of International Application No. PCT/SE2006/000398 (filed 3 Apr. 2006) which claims priority under 35U.S.C. §119(a)-(d) to Swedish Application No. 0500768-7 filed on 6 Apr. 2005 in Sweden.

FIELD OF THE INVENTION

The present invention discloses novel 5,7-disubstituted [1,3]thiazolo[4,5-d]pyrimidin-2(3H)-one derivatives together with processes for their preparation, pharmaceutical formulations comprising them and their use in therapy.

BACKGROUND OF THE INVENTION

Chemokines play an important role in immune and inflammatory responses in various diseases and disorders, including asthma, atherosclerosis and allergic diseases, as well as autoimmune pathologies such as rheumatoid arthritis and multiple sclerosis. These small, secreted molecules are a growing superfamily of 8-14 kDa proteins characterised by a conserved cysteine motif. At the present time, the chemokine superfamily comprises four groups exhibiting characteristic structural motifs, the C—X—C, C—C and C—X$_3$—C and XC families. The C—X—C and C—C families have sequence similarity and are distinguished from one another on the basis of a single amino acid insertion between the NH-proximal pair of cysteine residues. The C—X$_3$—C family is distinguished from the other two families on the basis of having a triple amino acid insertion between the NH-proximal pair of cysteine residues. In contrast, members of the XC family lack one of the first two cysteine residues.

The C—X—C chemokines include several potent chemoattractants and activators of neutrophils such as interleukin-8 (IL-8) and neutrophil-activating peptide 2 (NAP-2).

The C—C chemokines include potent chemoattractants of monocytes, lymphocytes and neutrophils. Examples include human monocyte chemotactic proteins 1-3 (MCP-1, MCP-2 and MCP-3), RANTES (Regulated on Activation, Normal T-cell-Expressed and Secreted), eotaxin and the macrophage inflammatory proteins 1α and 1β (MIP-1α and MIP-1β).

The C—X$_3$—C chemokine (also known as fractalkine) is a potent chemoattractant and activator of microglia in the central nervous system (CNS) as well as of monocytes, T cells, NK cells and mast cells.

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and CX$_3$CR1 for the C—X$_3$—C family. These receptors represent good targets for drug development since agents that modulate these receptors would be useful in the treatment of disorders and diseases such as those mentioned above.

WO 01/25242 discloses certain thiazolo[4,5-d]pyrimidine derivatives that are useful as antagonists of receptors linked to the C—X—C and C—C chemokine families, particularly as antagonists of the CXCR2 receptor.

The present invention relates to a group of compounds that are within the generic scope of WO 01/25242 but are of a structural type not specifically exemplified therein. When compared to the Examples disclosed in WO 01/25242, the compounds of the present invention display surprisingly useful properties as antagonists of the CX$_3$CR1 receptor.

DISCLOSURE OF THE INVENTION

The present invention provides compounds of formula (I)

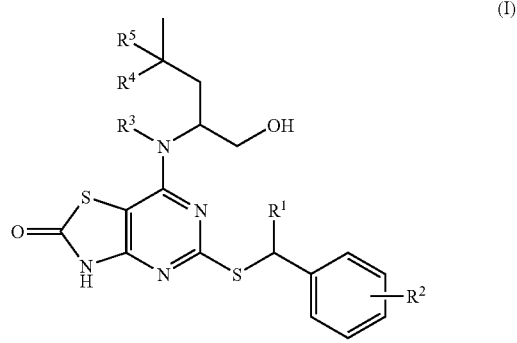

wherein:
$R^1$ represents CH$_3$ or CH$_3$CH$_2$;
$R^2$ represents H, 3-CN, 2-CF$_3$, 2-F, 3-F, 3-CF$_3$, 3-CONH$_2$ or 3-SO$_2$CH$_3$;
$R^3$ represents H;
$R^4$ represents H or CH$_3$; and
$R^5$ represents H; or, when $R^4$ is CH$_3$, $R^5$ represents H or F;
and pharmaceutically acceptable salts thereof.

The compounds of formula (I) may exist in stereoisomeric and/or tautomeric forms. It is to be understood that all enantiomers, diastereomers, racemates, tautomers and mixtures thereof are included within the scope of the invention.

In one embodiment, $R^1$ represents CH$_3$. In another embodiment, $R^1$ represents CH$_3$CH$_2$.

In one embodiment, $R^2$ represents H, 3-CN, 2-F, 3-F or 3-SO$_2$CH$_3$. In another embodiment, $R^2$ represents H. In another embodiment, $R^2$ represents 3-CN. In another embodiment, $R^2$ represents 2-F. In another embodiment, $R^2$ represents 3-SO$_2$CH$_3$.

In one embodiment, $R^4$ represents CH$_3$. In another embodiment, $R^4$ represents H.

In one embodiment, $R^5$ represents H.

In one embodiment, $R^1$ represents CH$_3$ and $R^5$ represents F.
In one embodiment, $R^1$ represents CH$_3$ and $R^5$ represents H.

In one embodiment, $R^1$ represents CH$_3$; $R^2$ represents H, 3-CN, 2-F or 3-SO$_2$CH$_3$; $R^4$ represents H; and $R^5$ represents H.

In one embodiment, $R^1$ represents CH$_3$; $R^2$ represents H, 3-CN, 2-F or 3-SO$_2$CH$_3$; $R^4$ represents CH$_3$; and $R^5$ represents H.

In another embodiment, $R^1$ represents CH$_3$; $R^2$ represents H; $R^4$ represents H or CH$_3$; and $R^5$ represents H.

In another embodiment, $R^1$ represents CH$_3$; $R^2$ represents 3-CN; $R^4$ represents H or CH$_3$; and $R^5$ represents H.

In another embodiment, $R^1$ represents CH$_3$; $R^2$ represents 2-F; $R^4$ represents H or CH$_3$; and $R^5$ represents H.

In another embodiment, R¹ represents CH₃; R² represents H, 2-F or 3-CN; R³ represents H; R⁴ represents H or CH₃; and R⁵ represents H.

In one embodiment, R¹ represents CH₃; R² represents 3-SO₂CH₃; R⁴ represents H or CH₃; and R⁵ represents H.

Particular compounds of formula (I) include:

7-{[(1R)-1-(hydroxymethyl)-3-methylbutyl]amino}-5-({(1R)-1-[3-(methylsulfonyl)phenyl]ethyl}thio)[1,3]thiazolo[4,5-d]pyrimidin-2(3H)-one;

7-{[(1R)-1-(hydroxymethyl)-3-methylbutyl]amino}-5-({1-[3-(trifluoromethyl)phenyl]ethyl}thio)[1,3]thiazolo[4,5-d]pyrimidin-2(3H)-one;

7-{[(1R)-1-(hydroxymethyl)butyl]amino}-5-{[(1S)-1-phenylethyl]thio}[1,3]thiazolo[4,5-d]pyrimidin-2(3H)-one;

7-{[(1R)-1-(hydroxymethyl)-3-methylbutyl]amino}-5-({(1S)-1-[3-(methylsulfonyl)phenyl]ethyl}thio)[1,3]thiazolo[4,5-d]pyrimidin-2(3H)-one;

7-{[(1R)-1-(hydroxymethyl)-3-methylbutyl]amino}-5-({1-[3-(trifluoromethyl)phenyl]ethyl}thio)[1,3]thiazolo[4,5-d]pyrimidin-2(3H)-one;

7-{[(1R)-1-(hydroxymethyl)-3-methylbutyl]amino}-5-({1-[2-(trifluoromethyl)phenyl]ethyl}thio)[1,3]thiazolo[4,5-d]pyrimidin-2(3H)-one;

7-{[(1R)-1-(hydroxymethyl)-3-methylbutyl]amino}-5-({1-[2-(trifluoromethyl)phenyl]ethyl}thio)[1,3]thiazolo[4,5-d]pyrimidin-2(3H)-one;

7-{[(1R)-1-(hydroxymethyl)butyl]amino}-5-({(is)-1-[3-(methylsulfonyl)phenyl]ethyl}thio)[1,3]thiazolo[4,5-d]pyrimidin-2(3H)-one;

7-{[(1R)-1-(hydroxymethyl)-3-methylbutyl]amino}-5-[(1-phenylethyl)thio][1,3]thiazolo[4,5-d]pyrimidin-2(3H)-one;

7-{[(1R)-1-(hydroxymethyl)-3-methylbutyl]amino}-5-{[(1R)-1-phenylethyl]thio}[1,3]thiazolo[4,5-d]pyrimidin-2(3H)-one;

7-{[(1R)-1-(hydroxymethyl)-3-methylbutyl]amino}-5-{[(is)-1-phenylethyl]thio}[1,3]thiazolo[4,5-d]pyrimidin-2(3H)-one;

3-{(1S)-1-[(7-{[(1R)-1-(hydroxymethyl)butyl]amino}-2-oxo-2,3-dihydro[1,3]thiazolo[4,5-d]pyrimidin-5-yl)thio]ethyl}benzonitrile;

7-{[(1R)-1-(hydroxymethyl)-3-methylbutyl]amino}-5-({1-[3-(methylsulfonyl)phenyl]ethyl}thio)[1,3]thiazolo[4,5-d]pyrimidin-2(31)-one;

3-{(1S)-1-[(7-{[(1R)-1-(Hydroxymethyl)-3-methylbutyl]amino}-2-oxo-2,3-dihydro[1,3]thiazolo[4,5-d]pyrimidin-5-yl)thio]ethyl}benzamide;

3-{(1R)-1-[(7-{[(1R)-1-(Hydroxymethyl)-3-methylbutyl]amino}-2-oxo-2,3-dihydro[1,3]thiazolo[4,5-d]pyrimidin-5-yl)thio]ethyl}benzamide;

7-{[(1R)-1-(hydroxymethyl)-3-methylbutyl]amino}-5-[(1-phenylpropyl)thio][1,3]thiazolo[4,5-d]pyrimidin-2(3H)-one;

5-{[(1S)-1-(2-fluorophenyl)ethyl]thio}-7-{[(1R)-1-(hydroxymethyl)-3-methylbutyl]amino}[1,3]thiazolo[4,5-d]pyrimidin-2(3H)-one;

3-{(1S)-1-[(7-{[(1R)-1-(hydroxymethyl)-3-methylbutyl]amino}-2-oxo-2,3-dihydro[1,3]thiazolo[4,5-d]pyrimidin-5-yl)thio]ethyl}benzonitrile;

7-{[(1R)-3-fluoro-1-(hydroxymethyl)-3-methylbutyl]amino}-5-{[(1S)-1-(2-fluorophenyl)ethyl]thio}[1,3]thiazolo[4,5-d]pyrimidin-2(3H)-one;

5-{[(1S)-1-(2-fluorophenyl)ethyl]thio}-7-{[(1R)-1-(hydroxymethyl)butyl]amino}[1,3]thiazolo[4,5-d]pyrimidin-2(3H)-one;

5-{[(1S)-1-(3-fluorophenyl)ethyl]thio}-7-{[(1R)-1-(hydroxymethyl)-3-methylbutyl]amino}[1,3]thiazolo[4,5-d]pyrimidin-2(3H)-one;

and pharmaceutically acceptable salts thereof.

When compared to the compounds disclosed in WO 01/25242, the compounds of the present invention are characterised by the presence of the branched thiobenzyl group at the 5-position of the thiazolopyrimidine ring system. That is, the compounds of the present invention incorporate a R¹ group that is not hydrogen.

According to the invention, we further provide a process for the preparation of a compound of formula (I), or a pharmaceutically acceptable salt thereof, which comprises:

a) reacting a compound of formula (II):

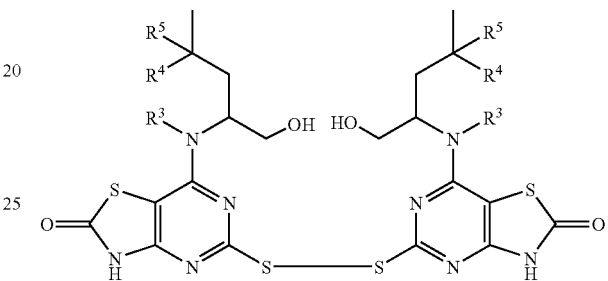

(II)

wherein R³, R⁴ and R⁵ are as defined in formula (I);
with a compound of formula (III):

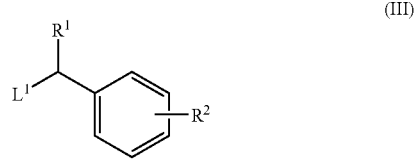

(III)

wherein R¹ and R² are as defined in formula (I) and L¹ represents a leaving group; or b) hydrolysing a compound of formula (IV)

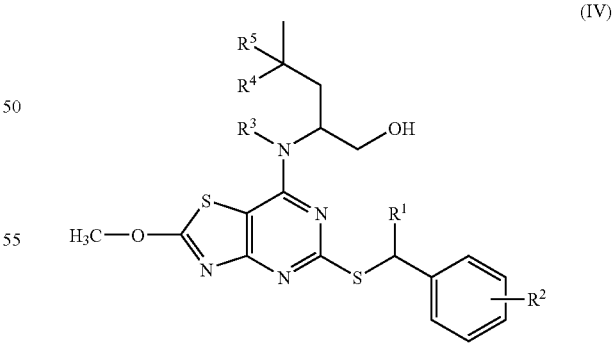

(IV)

wherein R¹, R², R³, R⁴ and R⁵ are as defined in formula (I); and where necessary converting the resultant compound of formula (I), or another salt thereof, into a pharmaceutically acceptable salt thereof; or converting the resultant compound of formula (I) into a further compound of formula (I); and where desired converting the resultant compound of formula (I) into an optical isomer thereof.

In process (a), the reactants (II) and (III) are coupled together in a suitable organic solvent such as dimethylsulfoxide (DMSO), acetonitrile or 1-methyl-2-pyrrolidinone (NMP). The reaction is optionally performed in the presence of an added organic or inorganic base such as triethylamine, N,N-diisopropylethylamine (DIPEA) or sodium hydride. The reaction is performed in the presence of a mild reducing agent such a sodium borohydride. The reaction is conducted at a suitable temperature, normally between room temperature and the boiling point of the solvent. The reaction is generally continued for a period of about one hour to one week, or until analysis indicates that formation of the required product is complete. A suitable leaving groups $L^1$ is halogen, particularly chloro or bromo. In one embodiment, $L^1$ represents chloro.

In process (b), the reactant (IV) is subjected to acid catalysed hydrolysis in a suitable organic solvent such as dioxane, tetrahydrofuran (THF), dimethylsulphoxide or 1-methyl-2-pyrrolidinone. Suitable acids include inorganic acids such as hydrochloric acid or hydrobromic acid, or strong organic acids such as trifluoroacetic acid. The reaction is conducted at a suitable temperature, normally between room temperature and the boiling point of the solvent. The reaction is generally continued for a period of about one hour to one day, or until analysis indicates that formation of the required product is complete.

It will be apparent to a person skilled in the art that in the above processes it may be desirable or necessary to protect an amine, hydroxyl or other potentially reactive group. Suitable protecting groups and details of processes for adding and removing such groups are, in general, well known in the art. See, for example, "Protective Groups in Organic Synthesis", 3rd Edition (1999) by Greene and Wuts.

The present invention includes compounds of formula (I) in the form of salts. Suitable salts include those formed with organic or inorganic acids or organic or inorganic bases. Such salts will normally be pharmaceutically acceptable although salts of non-pharmaceutically acceptable acids or bases may be of utility in the preparation and purification of the compound in question.

Salts of compounds of formula (I) may be formed by reacting the free compound, or a salt, enantiomer or racemate thereof, with one or more equivalents of the appropriate acid or base. The reaction may be carried out in a solvent or medium in which the salt is insoluble or in a solvent in which the salt is soluble, for example, water, dioxan, ethanol, tetrahydrofuran or diethyl ether, or a mixture of solvents, which may be removed in vacuo or by freeze drying. The reaction may also be a metathetical process or it may be carried out on an ion exchange resin.

Compounds of formula (II) may, in general, be prepared using known methods that will be readily apparent to the man skilled in the art. One such suitable route is shown in the following Scheme.

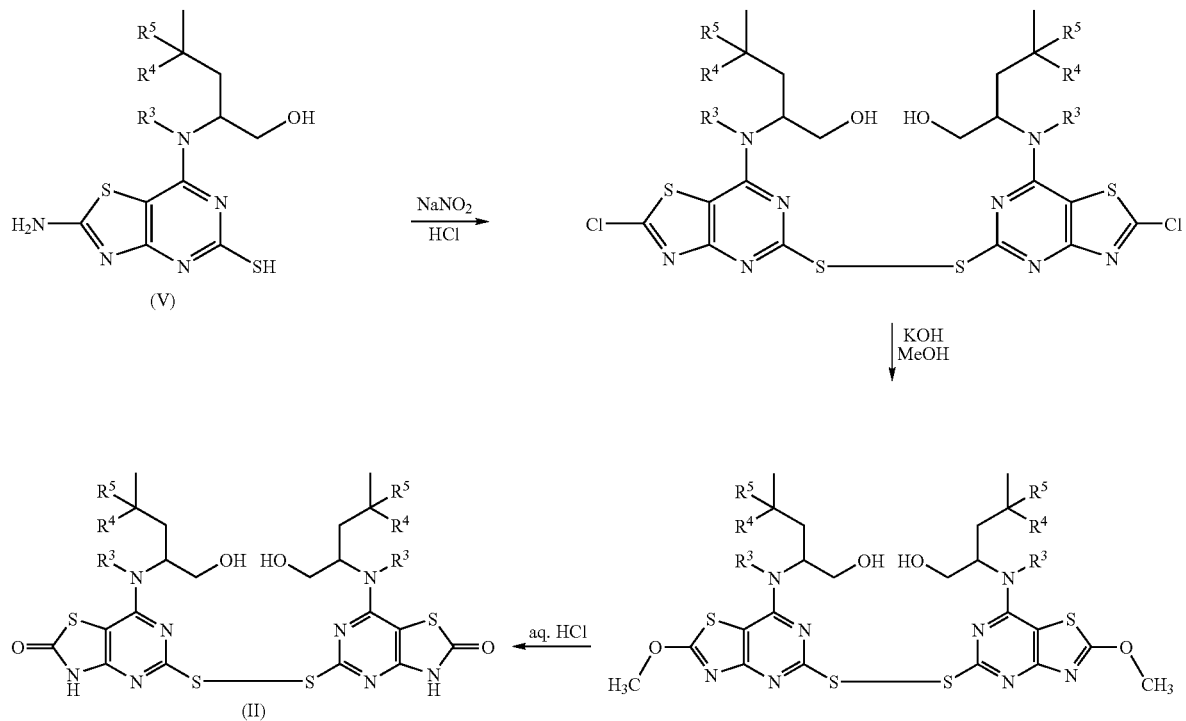

Compounds of formulae (III) are either commercially available, or known in the literature, or may be prepared using known methods that will be readily apparent to the man skilled in the art.

Compounds of formula (IV) are either known from WO 01/25242 or may be prepared using known methods that will be readily apparent to the man skilled in the art. One such suitable route is shown in the following Scheme.

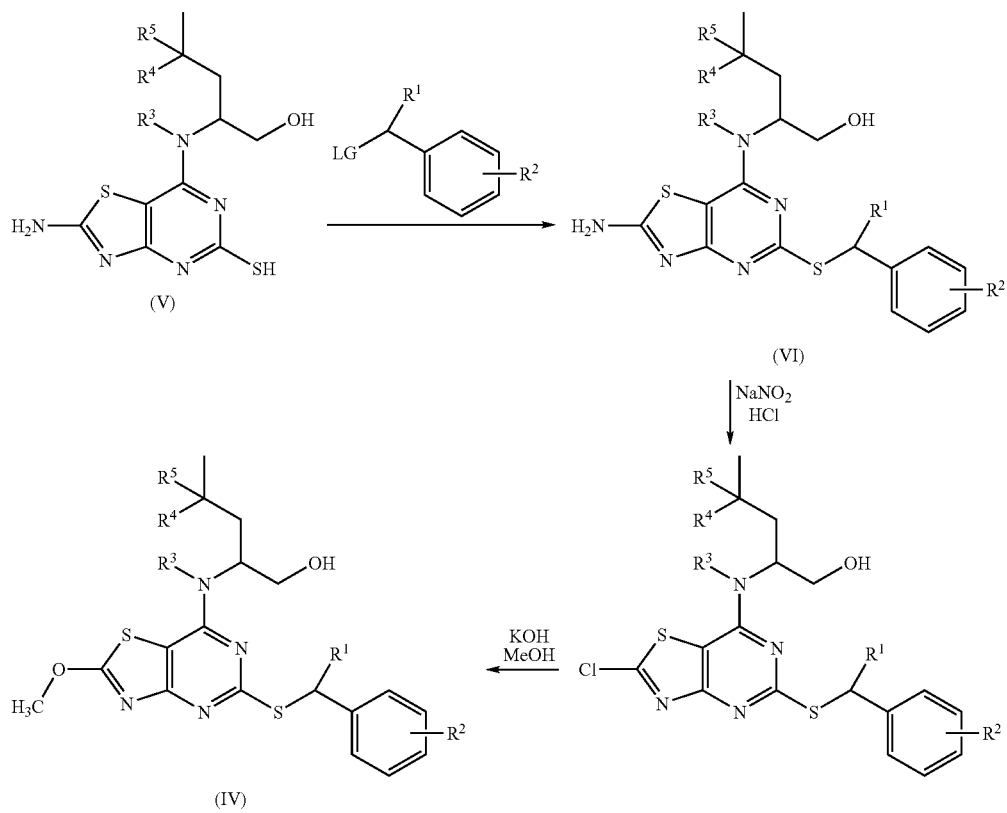

Compounds of formula (V) are either known from WO 00/09511 or may be prepared using known methods that will be readily apparent to the man skilled in the art.

For example, compounds of formula (V), and thence those of formula (VI), may be prepared as shown in the following Scheme:

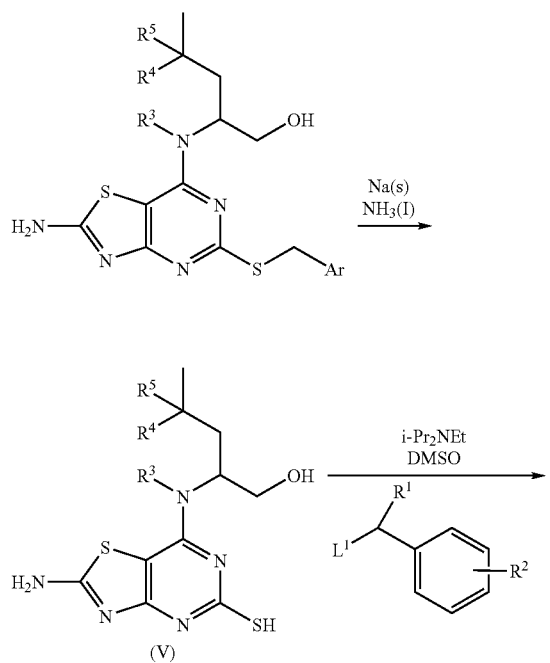

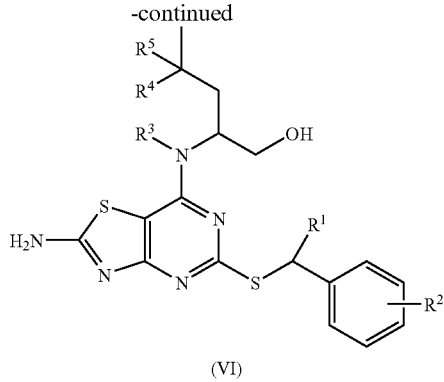

Suitable specific methods for the preparation of compounds of formulae (II), (III), (IV), (V) and (VI) are detailed in the Examples section of the present application and such methods represent specific embodiments of the processes of the invention.

Intermediate compounds may be used as such or in protected form. Suitable protecting groups and details of processes for adding and removing such groups are, in general, well known in the art. See, for example, "Protective Groups in Organic Synthesis", 3rd Edition (1999) by Greene and Wuts.

The compounds of the invention and intermediates thereto may be isolated from their reaction mixtures and, if necessary further purified, by using standard techniques.

The compounds of formula (I) may exist in stereoisomeric forms. Therefore, all enantiomers, diastereomers, racemates and mixtures thereof are included within the scope of the invention. The various optical isomers may be isolated by separation of a stereoisomeric mixture of the compounds using conventional techniques, for example, fractional crystallisation, or HPLC. Alternatively, the various optical isomers may be prepared directly using optically active starting materials.

The compounds of formula (I) contain two stereogenic centres and may thus exist in four discrete stereoisomeric forms as shown in formulae (Ia) to (Id)

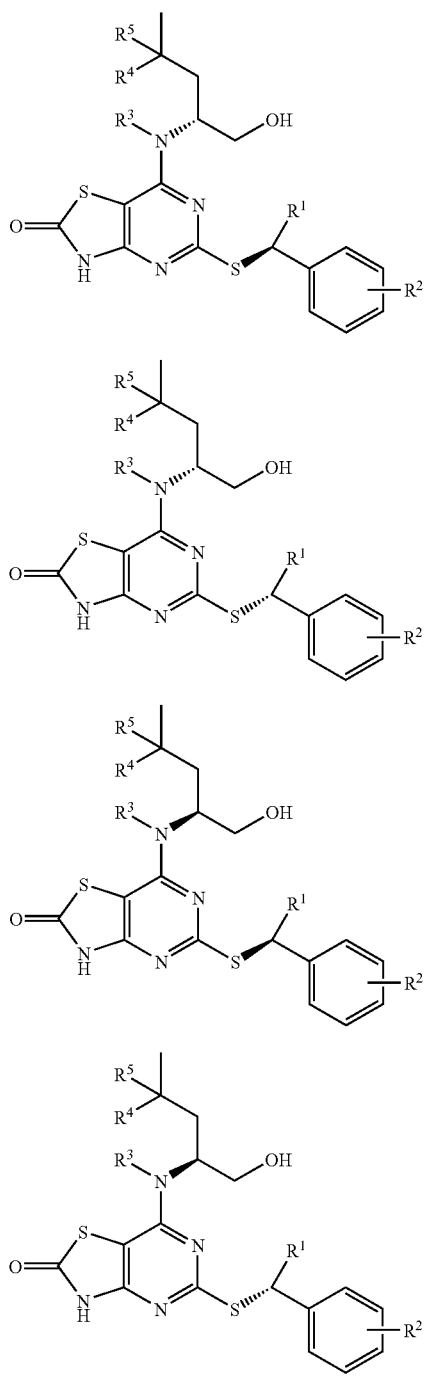

All such four stereoisomers and any mixtures thereof are included within the scope of the invention. In one embodiment, the compounds of formula (I) have the stereochemistry shown in formula (Ia). In another embodiment, the compounds of formula (I) have the stereochemistry shown in formula (Ib).

Intermediate compounds may also exist in stereoisomeric forms and may be used as purified enantiomers, diastereomers, racemates or mixtures.

The compounds of formula (I), and their pharmaceutically acceptable salts are useful because they possess pharmacological activity as antagonists of the $CX_3CR1$ receptor. In particular, when compared to the compounds specifically exemplified in WO 01/25242, the compounds of formula (I) of the present invention possess significantly improved potencies for inhibition of the $CX_3CR1$ receptor and/or decreased potencies for inhibition of the CXCR2 receptor. Preferred compounds of the present invention display both enhanced potency for the inhibition of $CX_3CR1$ and decreased potency for inhibition of CXCR2.

In one aspect the present invention provides a compound of formula (I) or a pharmaceutically acceptable salt thereof, for use as a medicament.

In another aspect the present invention provides the use of a compound of formula (I) or a pharmaceutically acceptable salt thereof, in the manufacture of a medicament, for the treatment or prophylaxis of diseases or conditions in which antagonism of the $CX_3CR1$ receptor is beneficial.

In another aspect the present invention provides the use of a compound of formula (I) or a pharmaceutically acceptable salt thereof, in the manufacture of a medicament, for the treatment or prophylaxis of neurodegenerative disorders, demyelinating disease, cardio- and cerebrovascular atherosclerotic disorders, peripheral artery disease, rheumatoid arthritis, pulmonary diseases such as COPD, asthma or pain.

In another aspect the present invention provides the use of a compound of formula (I) or a pharmaceutically acceptable salt thereof, in the manufacture of a medicament, for the treatment or prophylaxis of multiple sclerosis (MS).

In another aspect the present invention provides the use of a compound of formula (I) or a pharmaceutically acceptable salt thereof, in the manufacture of a medicament, for the treatment or prophylaxis of atherosclerosis by preventing and/or reducing the formation of new atherosclerotic lesions or plaques and/or by preventing or slowing progression of existing lesions and plaques.

In another aspect the present invention provides the use of a compound of formula (I) or a pharmaceutically acceptable salt thereof, in the manufacture of a medicament, for the treatment or prophylaxis of atherosclerosis by changing the composition of the plaques to reduce the risk of plaque rupture and atherothrombotic events.

According to the invention, there is also provided a method of treating, or reducing the risk of, diseases or conditions in which antagonism of the $CX_3CR1$ receptor is beneficial which comprises administering to a person suffering from or at risk of, said disease or condition, a therapeutically effective amount of a compound of formula (I) or a pharmaceutically acceptable salt thereof.

There is also provided a method of treating, or reducing the risk of, neurodegenerative disorders, demyelinating disease, cardio- and cerebrovascular atherosclerotic disorders, peripheral artery disease, rheumatoid arthritis, pulmonary diseases such as COPD, asthma or pain in a person suffering from or at risk of, said disease or condition, wherein the method comprises administering to the person a therapeutically effective amount of a compound of formula (I) or a pharmaceutically acceptable salt thereof.

There is also provided a method of treating, or reducing the risk of, multiple sclerosis (MS) in a person suffering from or at risk of, said disease or condition, wherein the method comprises administering to the person a therapeutically effective amount of a compound of formula (I) or a pharmaceutically acceptable salt thereof.

There is also provided a method of treating, or reducing the risk of atherosclerosis by preventing and/or reducing the formation of new atherosclerotic lesions or plaques and/or by preventing or slowing progression of existing lesions and plaques in a person suffering from or at risk of, said disease or condition, wherein the method comprises administering to the person a therapeutically effective amount of a compound of formula (I) or a pharmaceutically acceptable salt thereof.

There is also provided a method of treating, or reducing the risk of atherosclerosis by changing the composition of the plaques so as to reduce the risk of plaque rupture and atherothrombotic events in a person suffering from or at risk of, said disease or condition, wherein the method comprises administering to the person a therapeutically effective amount of a compound of formula (I) or a pharmaceutically acceptable salt thereof.

In another aspect the invention provides a pharmaceutical formulation comprising a therapeutically effective amount of a compound of formula (I), or a pharmaceutically acceptable salt thereof, in admixture with a pharmaceutically acceptable adjuvant, diluent or carrier, for use in the treatment or prophylaxis of diseases or conditions in which antagonism of the $CX_3CR1$ receptor is beneficial.

In another aspect the invention provides a pharmaceutical formulation comprising a therapeutically effective amount of a compound of formula (I), or a pharmaceutically acceptable salt thereof, in admixture with a pharmaceutically acceptable adjuvant, diluent or carrier, for use in the treatment or prophylaxis of neurodegenerative disorders, demyelinating disease, cardio- and cerebrovascular atherosclerotic disorders, peripheral artery disease, rheumatoid arthritis, COPD, asthma or pain.

In another aspect the invention provides a pharmaceutical formulation comprising a therapeutically effective amount of a compound of formula (I), or a pharmaceutically acceptable salt thereof, in admixture with a pharmaceutically acceptable adjuvant, diluent or carrier, for use in the treatment or prophylaxis of multiple sclerosis.

In another aspect the present invention provides a pharmaceutical formulation comprising a therapeutically effective amount of a compound of formula (I), or a pharmaceutically acceptable salt thereof, in admixture with a pharmaceutically acceptable adjuvant, diluent or carrier, for use in the treatment or prophylaxis of atherosclerosis by preventing and reducing the formation of new atherosclerotic lesions and/or plaques and/or by preventing or slowing progression of existing lesions and plaques.

In another aspect the present invention provides a pharmaceutical formulation comprising a therapeutically effective amount of a compound of formula (I), or a pharmaceutically acceptable salt thereof, in admixture with a pharmaceutically acceptable adjuvant, diluent or carrier, for use in the treatment or prophylaxis of atherosclerosis by changing the composition of the plaques so as to reduce the risk of plaque rupture and atherothrombotic events.

The compounds of formula (I) and their pharmaceutically acceptable salts are indicated for use in the treatment or prophylaxis of diseases or conditions in which modulation of activity at the $CX_3CR1$ receptor is desirable. In particular, the compounds are indicated for use in the treatment of neurodegenerative disorders or demyelinating disease in mammals including man. More particularly, the compounds are indicated for use in the treatment of multiple sclerosis. The compounds are also indicated to be useful in the treatment of pain, rheumatoid arthritis, osteoarthritis, cardio- and cerebrovascular atherosclerotic disorders, peripheral artery disease and pulmonary arterial hypertension.

Conditions that may be specifically mentioned are: neurodegenerative diseases and dementia disorders, for example, Alzheimer's disease, amyotrophic lateral sclerosis and other motor neuron diseases, Creutzfeldt-Jacob's disease and other prion diseases, HIV encephalopathy, Huntington's disease, frontotemporal dementia, Lewy body dementia and vascular dementia; polyneuropathies, for example, Guillain-Barré syndrome, chronic inflammatory demyelinating polyradiculoneuropathy, multifocal motor neuropathy and plexopathies; CNS demyelination, for example, acute disseminated/haemorrhagic encephalomyelitis and subacute sclerosing panencephalitis; neuromuscular disorders, for example, myasthenia gravis and Lambert-Eaton syndrome; spinal disorders, for example, tropical spastic paraparesis and stiff-man syndrome; paraneoplastic syndromes, for example, cerebellar degeneration and encephalomyelitis; traumatic brain injury; migraine; cancer; allograft rejection; systemic sclerosis; viral infections; parasite-transmitted diseases, for example, malaria; periodontal disease; myocardial infarction; stroke; coronary heart disease; ischaemic heart disease; and restenosis; rheumatoid arthritis; pulmonary diseases such as COPD; asthma or pain.

The compounds of the invention are also indicated for use in the treatment of atherosclerosis by preventing and/or reducing the formation of new atherosclerotic lesions or plaques and/or by preventing or slowing progression of existing lesions and plaques.

The compounds of the invention are also indicated for use in the treatment of atherosclerosis by changing the composition of the plaques so as to reduce the risk of plaque rupture and atherothrombotic events.

The compounds of the invention are also indicated for use in the treatment of inflammatory bowel disease (IBD), for example, Crohn's disease and ulcerative colitis, by inducing remission and/or maintaining remission of IBD.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

For the above mentioned therapeutic indications, the dosage administered will, of course, vary with the compound employed, the mode of administration and the treatment desired. However, in general, satisfactory results are obtained when the compounds are administered at a dosage of the solid form of between 1 mg and 2000 mg per day.

The compounds of formula (I) and pharmaceutically acceptable derivatives thereof, may be used on their own, or in the form of appropriate pharmaceutical compositions in which the compound or derivative is in admixture with a pharmaceutically acceptable adjuvant, diluent or carrier. Administration may be by, but is not limited to, enteral (including oral, sublingual or rectal), intranasal, intravenous, topical or other parenteral routes. Conventional procedures for the selection and preparation of suitable pharmaceutical formulations are described in, for example, "Pharmaceuticals—The Science of Dosage Form Designs", M. E. Aulton, Churchill Livingstone, 1988. The pharmaceutical composition preferably comprises less than 80% and more preferably less than 50% of a compound of formula (I), or a pharmaceutically acceptable salt thereof.

There is also provided a process for the preparation of such a pharmaceutical composition that comprises mixing the ingredients.

The compounds of formula (I) and pharmaceutically acceptable derivatives thereof, may be used on their own, or in the form of appropriate pharmaceutical compositions in which the compound or derivative is in admixture with a pharmaceutically acceptable adjuvant, diluent is or carrier. Administration may be by, but is not limited to, enteral (including oral, sublingual or rectal), intranasal, intravenous, topical or other parenteral routes. Conventional procedures for the selection and preparation of suitable pharmaceutical formulations are described in, for example, "Pharmaceuticals—The Science of Dosage Form Designs", M. E. Aulton, Churchill Livingstone, 1988. The pharmaceutical composition preferably comprises less than 80% and more preferably less than 50% of a compound of formula (I), or a pharmaceutically acceptable salt thereof.

There is also provided a process for the preparation of such a pharmaceutical composition that comprises mixing the ingredients.

The invention further relates to combination therapies wherein a compound of formula (I) or a pharmaceutically acceptable salt thereof, or a pharmaceutical composition or formulation comprising a compound of formula (I), is administered concurrently or sequentially with therapy and/or an agent for the treatment of any one of cardio- and cerebrovascular atherosclerotic disorders and peripheral artery disease.

In particular, a compound of formula (I) or a pharmaceutically acceptable salt thereof may be administered in association with compounds from one or more of the following groups:

1) anti-inflammatory agents, for example,
   a) NSAIDs (e.g. acetylsalicylic acid, ibuprofen, naproxen, flurbiprofen, diclofenac, indometacin);
   b) leukotriene synthesis inhibitors (5-LO inhibitors e.g. AZD4407, Zileuton, licofelone, CJ13610, CJ13454; FLAP inhibitors e.g. BAY-Y-1015, DG-031, MK591, MK886, A81834; LTA4 hydrolase inhibitors e.g. SC56938, SC57461A);
   c) leukotriene receptor antagonists; (e.g. CP195543, amelubant, LY293111, accolate, MK571);
2) anti-hypertensive agents, for example,
   a) beta-blockers (e.g. metoprolol, atenolol, sotalol);
   b) angiotensin converting enzyme inhibitors (e.g. captopril, ramipril, quinapril, enalapril);
   c) calcium channel blockers (e.g. verapamil, diltiazem, felodipine, amlodipine);
   d) angiotensin II receptor antagonists (e.g. irbesartan, candesartan, telemisartan, losartan);
3) anti-coagulantia, for example,
   a) thrombin inhibitors (e.g. ximelagatran), heparines, factor Xa inhibitors;
   b) platelet aggregation inhibitors (e.g. clopidogrel, ticlopidine, prasugel, AZ4160);
4) modulators of lipid metabolism, for example,
   a) insulin sensitizers such as PPAR agonists (e.g. pioglitazone, rosiglitazone, Galida, muraglitazaar, gefemrozil, fenofibrate);
   b) HMG-CoA reductase inhibitors, statins (e.g. simvastatin, pravastatin, atorvaststin, rosuvastatin, fluvastatin, pitavastatin);
   c) cholesterol absorption inhibitors (e.g. ezetimibe);
   d) IBAT inhibitors (e.g. AZD-7806);
   e) LXR agonists (e.g. GW-683965A, T-0901317);
   f) FXR receptor modulators;
   g) phospholipase inhibitors;
5) anti-anginal agents, for example, nitrates and nitrites;
6) modulators of oxidative stress, for example, anti-oxidants. (probucol), myeloperoxidase inhibitors.

The invention is illustrated, but in no way limited, by the following examples:

General Methods

All solvents used were analytical grade and commercially available anhydrous solvents were routinely used for reactions. Reactions were typically run under an inert atmosphere of nitrogen or argon.

$^1$H and $^{13}$C NMR spectra were recorded at 400 MHz for proton and 100 MHz for carbon-13 either on a Varian Unity+ 400 NMR Spectrometer equipped with a 5 mm BBO probe with Z-gradients, or a Bruker Avance 400 NMR spectrometer equipped with a 60 µl dual inverse flow probe with Z-gradients, or a Bruker DPX400 NMR spectrometer equipped with a 4-nucleus probe equipped with Z-gradients. 600 MHz $^1$H NMR spectra were recorded on a Bruker av600 NMR spectrometer equipped with a 5 mm BBI probehead with Z-gradients. 300 MHz $^1$H NMR spectra were recorded on a Varian Gemini 300 NMR equipped with a 5 mm BBI probehead.

Unless specifically noted in the examples, spectra were recorded at 400 MHz for proton and 100 MHz for carbon-13. The following reference signals were used: the middle line of DMSO-$d_6$ δ 2.50 ($^1$H), δ 39.51 ($^{13}$C); the middle line of CD$_3$OD δ 3.31 ($^1$H) or δ 49.15 ($^{13}$C); acetone-$d_6$ 2.04 ($^1$H), 206.5 ($^{13}$C); and CDCl$_3$ $_\delta$ $_{7.26}$ ($^1$H), the middle line of CDCl$_3$ $_\delta$ 77.16 ($^{13}$C) (unless otherwise indicated).

Enantiomeric excess was determined by GC on a Cyclodex B column (isothermic elution 100° C.).

Mass spectra were recorded on a Waters LCMS consisting of an Alliance 2795 (LC) and a ZQ single quadrupole mass spectrometer. The mass spectrometer was equipped with an electrospray ion source (ESI) operated in a positive or negative ion mode. The capillary voltage was 3 kV and the mass spectrometer was scanned from m/z 100-700 with a scan time of 0.3 or 0.8 s. Separations were performed on either Waters X-Terra MS, C8-columns, (3.5 µm, 50 or 100 mm×2.1 mm i.d.), or a ScantecLab's ACE 3 AQ column (100 mm×2.1 mm i.d.). The column temperature was set to 40° C. A linear gradient was applied using a neutral or acidic mobile phase system, running at 0% to 100% organic phase in 4-5 minutes, flow rate 0.3 ml/min. Neutral mobile phase system: acetonitrile/[10 mM NH$_4$OAc (aq.)/MeCN (95:5)], or [10 mM NH$_4$OAc (aq.)/MeCN (1/9)]/[10 mM NH$_4$OAc (aq.)/MeCN (9/1)]. Acidic mobile phase system: [133 mM HCOOH (aq.)/MeCN (5/95)]/[8 mM HCOOH (aq.)/MeCN (98/2)].

Compound identification was performed on a GC-MS (GC 6890, 5973N MSD) supplied by Agilent Technologies. The column used was a VF-5 MS, ID 0.25 mm×30 m, 0.25 µm (Varian Inc.). A linear temperature gradient was applied starting at 40° C. (hold 1 min) and ending at 300° C. (hold 1 min), 25° C./minute. The MS was equipped with an EI ion source. The MS was scanned between m/z 50-500 and the scan speed was set to 3.25 scan/s. The electron voltage was set to 70 eV.

HPLC analyses were performed on an Agilent HEP1000 system consisting of G1379A Micro Vacuum Degasser, G1312A Binary Pump, G1367A Wellplate auto-sampler, G1316A Thermostatted Column Compartment and G1315B Diode Array Detector. Column: X-Terra MS, Waters, 4.6×50 mm, 3.5 µm. The column temperature was set to 40° C. and the flow rate to 1.5 ml/min. The Diode Array Detector was scanned from 210-300 nm, step and peak width were set to 2 nm and 0.05 min, respectively. A linear gradient was applied, run from 0% to 100% acetonitrile, in 4 min. Mobile phase: acetonitrile/10 mM ammonium acetate in 5% acetonitrile in MilliQ Water.

A typical workup procedure after a reaction consisted of extraction of the product with a solvent such as ethyl acetate, washing with water followed by drying of the organic phase over $MgSO_4$ or $Na_2SO_4$, and concentration of the solution in vacuo.

Thin layer chromatography (TLC) was performed on Merck TLC-plates (Silica gel 60 $F_{254}$) and UV was used to visualize the spots. Flash chromatography was preformed on a Combi Flash® Companion™ using RediSep™ normal-phase flash columns or on Merck Silica gel 60 (0.040-0.063 mm). Typical solvents used for flash chromatography were mixtures of chloroform/methanol, toluene/ethyl acetate and ethyl acetate/hexanes.

Preparative chromatography was run on a Gilson autopreparative HPLC with a diode array detector. Column: XTerra MS C8, 19×300 mm, 7 μm. Gradient with acetonitrile/0.1M ammonium acetate in 5% acetonitrile in MilliQ Water, run from 20% to 60% acetonitrile, in 13 min. Flow rate: 20 ml/min. Alternatively, purification was achieved on a semi preparative Shimadzu LC-8A HPLC with a Shimadzu SPD-10A UV-vis.-detector equipped with a Waters Symmetry column (C18, 5 μm, 100 mm×19 mm). Gradient with acetonitrile/0.1% trifluoroacetic acid in MilliQ Water, run from 35% to 60% acetonitrile in 20 min. Flow rate: 10 ml/min.

Recrystallization was typically performed in solvents or solvent mixtures such as ether, ethyl acetate/heptanes and methanol/water.

The following abbreviations have been used: DCM=dichloromethane; DIPCl=β-chlorodiisopinocamphenylborane (DIP-Chloride™); DIPEA=N,N-diisopropylethylamine; DMF=N,N-dimethylformamide; DMSO=dimethylsulfoxide; NCS=N-chlorosuccinimide; NMP=1-methyl-2-pyrrolidinone; THF=tetrahydrofuran; aq=aqueous; conc=concentrated.

Starting materials used were either available from commercial sources or prepared according to literature procedures and had experimental data in accordance to those reported. The following are examples of starting material that were prepared:

(2R)-2-[(2-amino-5-mercapto[1,3]thiazolo[4,5-d]pyrimidin-7-yl)amino]-4-methylpentan-1-ol: WO 02/076990;
5-(benzylthio)-7-chloro[1,3]thiazolo[4,5-d]pyrimidin-2-amine: WO 00/09511;
1-[3-(methylsulfonyl)phenyl]ethanone: T. Fujita, J. Iwasa and C. Hansch, *Journal of the American Chemical Society*, 1964, 86, 5175-5180;
3-[(1S)-1-hydroxyethyl]benzonitrile: Belley, M. *Bioorg. Med. Chem.*, 1999, 7, 2697-2704;
3-(methylsulfonyl)benzaldehyde: P. L Ornstein et al., *J. Med. Chem.*, 1998, Vol. 41, No. 3, 358-378;
3-(1-hydroxyethyl)benzamide: Watson, C. Y; Whish, W. J. D; Threadgill, M. D. *Bioorg. Med. Chem.* 1998 6(6) 721-34;
(1-chloropropyl)benzene: Desai, V. R.; Nechvatal, A.; Tedder, J. M. *J. Chem. Soc.* (B) 1969, 30-32.
(1S)-1-(2-fluorophenyl)ethanol: Garrett, C. E. *Tetrahedron: Asymmetry* 2002, 13, 1347-1349; Doucet, H. *Chem. Eur. J.* 1999, 5, 1320-1330;
(2R)-2-amino-4-fluoro-4-methylpentan-1-ol: Truong, V. L; Gauthier, J. Y; Boyd, M; Roy, B; Scheigetz, J. *Synlett* 2005, 8, 1279-1280; following the route for the S enantiomer:
(1S)-1-(3-fluorophenyl)ethanol: Pastor, I. M. *Chem. Eur. J.* 2003, 9, 4031-4045.

In the general methods that follow, R represents H or $CH_3$, R' represents H or F; and Ar represents phenyl substituted by $R^2$ wherein $R^2$ is as defined in formula (I).

General Method A

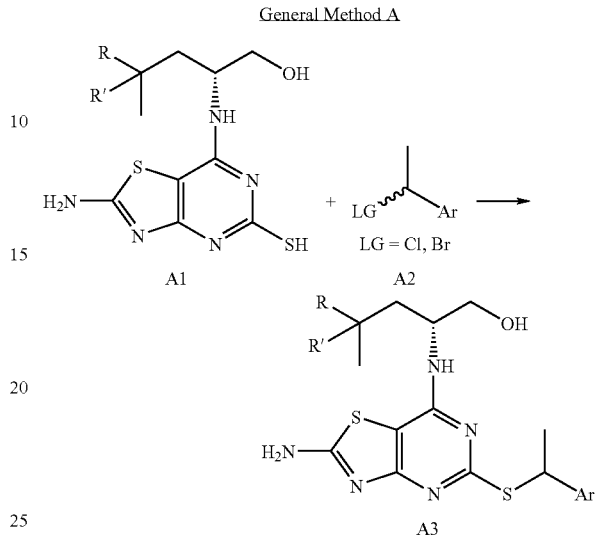

Sodium borohydride (0.1 equiv.), DIPEA (1.5 equiv.) and A2 (1.2 equiv.) were added A1 (1.0 equiv.) in DMSO under a nitrogen atmosphere. The resulting reaction mixture was stirred at 40° C. until the reaction was complete (monitored by LC-MS, HPLC or TLC). The mixture was poured into ice water and the product was extracted with DCM or EtOAc. The combined organic phases were dried and concentrated in vacuo. The crude product was, if necessary, purified using preparative HPLC or by flash column chromatography.

General Method B

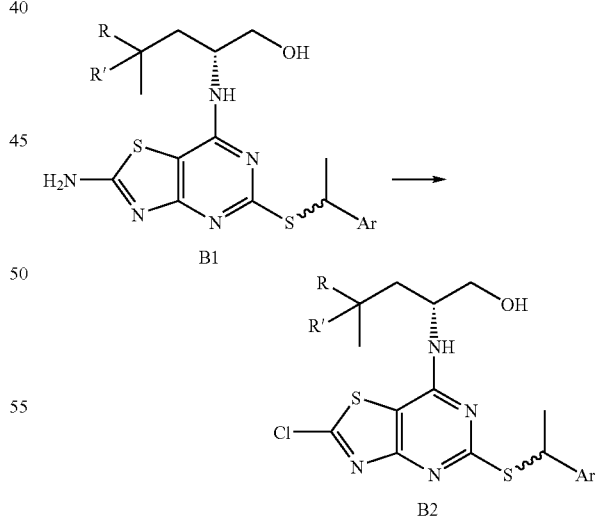

Conc. HCl (2.5 mL/mmol Bi) was added to Bi (1.0 equiv.) in $CH_3CN$. The reaction mixture was cooled in an ice bath and sodium nitrite (2.0 equiv.) dissolved in a minimal amount of water was added dropwise. The reaction was stirred at 0° C. until the reaction was complete (monitored by LC-MS, HPLC or TLC) and was then poured into ice water, neutralized with sodium bicarbonate and extracted with DCM or EtOAc. The combined organic phases were dried and concentrated in vacuo to give the product.

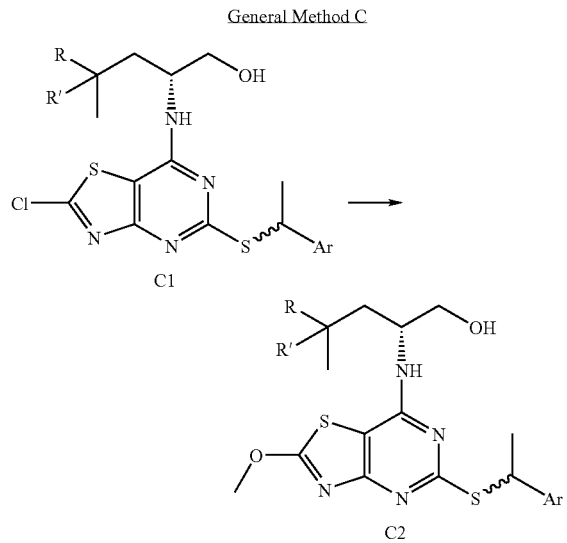

Potassium hydroxide (2.0 equiv.) dissolved in methanol was added dropwise to a cooled (0° C.) solution of C1 (1.0 equiv.) in methanol. The resulting mixture was stirred at 0° C. until the reaction was complete (monitored by LC-MS, HPLC or TLC). The solvent was evaporated off and the product was used in the next reaction step without further purification.

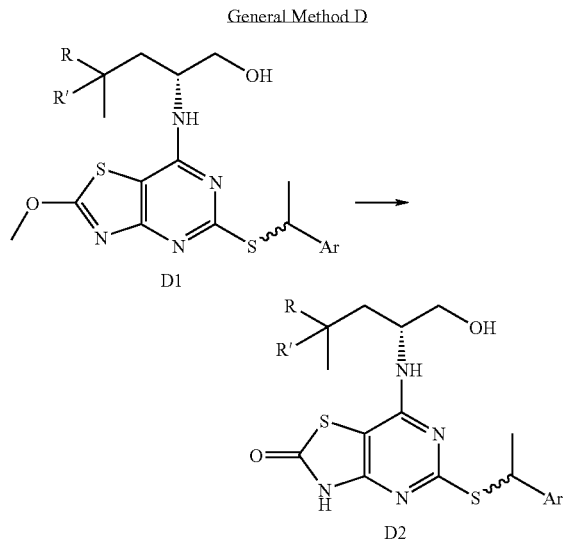

A solution of concentrated HCl (1.0 equiv.) was added to a cooled (0° C.) solution of D1 (1.0 equiv.) in 1,4-dioxane. The resulting mixture was stirred at 40° C. until the reaction was complete (monitored by LC-MS, HPLC or TLC). The reaction mixture was neutralised with saturated NaHCO$_3$ (aq) and the dioxane was evaporated off. The residue was dissolved in DCM or EtOAc, washed with brine, dried and concentrated in vacuo. The crude product was, if necessary, purified using preparative HPLC or by flash column chromatography.

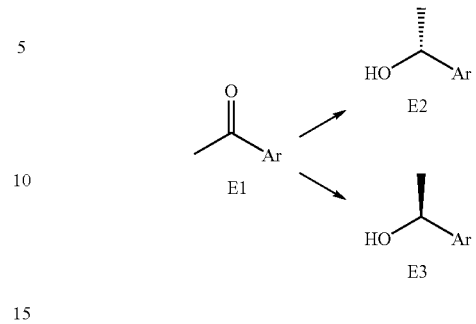

E1 (1.0 equiv.) in THF was added at 0° C. to (+)-DIPCl (to give E2) or (−)-DIPCl (to give E3) (1.5 equiv.) in THF under an argon atmosphere. The reaction mixture was allowed to slowly reach room temperature overnight. The solvent was evaporated off followed by the addition of Et$_2$O and diethanolamine (2.2 equiv.). The mixture was stirred until the reaction was complete (monitored by LC-MS, HPLC or TLC). The precipitate that formed was filtered off, washed with Et$_2$O and the filtrate was concentrated in vacuo. The crude product was, if necessary, purified using preparative HPLC or by flash column chromatography.

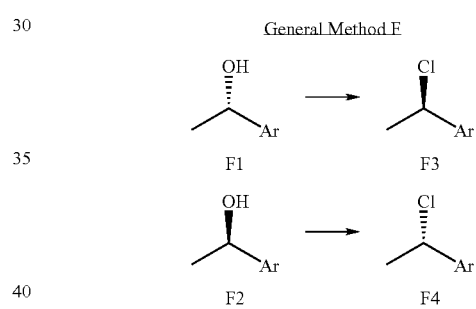

Triphenyl phosphine (1.3 equiv.) in THF was added at 0° C. to NCS (1.3 equiv.) in THF under an argon atmosphere. The resulting mixture was stirred at ambient temperature for 30 min. F1 or F2 (1 equiv.) was added at 0° C. and the reaction mixture was stirred at ambient temperature until the reaction was complete (monitored by LC-MS, HPLC or TLC). The solvent was evaporated off followed by addition of hexane and removal of the precipitate by filtration. The filtrate was concentrated in vacuo and the crude product was, if necessary, purified using preparative HPLC or by flash column chromatography.

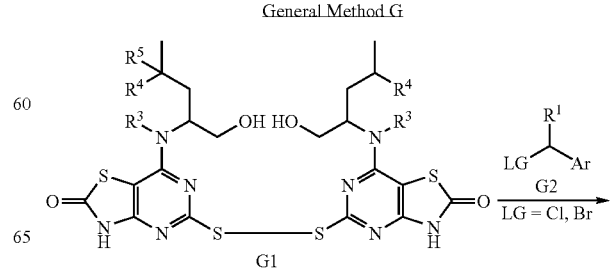

-continued

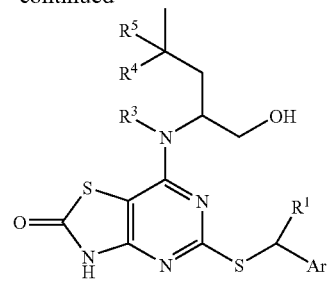

Sodium borohydride (1 to 2 equiv.) was added to G1 (1.0 equiv.) in DMSO. Once effervescence had ceased, G2 (1.2 equiv.) was added. The resulting reaction mixture was stirred at 40° C. until the reaction was complete (monitored by LC-MS, HPLC or TLC). Purification, if necessary, was achieved using preparative HPLC or by flash column chromatography.

EXAMPLE 1

7-{[(1R)-1-(Hydroxymethyl)-3-methylbutyl]amino}-5-({(1R)-1-[3-(methylsulfonyl)phenyl]ethyl}thio)[1,3]thiazolo[4,5-d]pyrimidin-2(3H)-one a) (1R)-1-[3-(Methylsulfonyl)phenyl]ethanol B(OMe)$_3$ (62 μL, 0.55 mmol) was added to (R)-(+)-α,α-diphenyl-2-pyrrolidinemethanol in THF (5 mL) followed by BH$_3$.Me$_3$S (2M in THF, 1.23 mL, 2.54 mmol). The mixture was stirred for 1 h before 1-[3-(methylsulfonyl)phenyl]ethanone (458 mg, 2.31 mmol) in THF (5 mL) was added over 1.5 h. The resulting mixture was stirred overnight and then quenched with 1M HCl (2 mL). The mixture was concentrated and the crude product was purified by flash column chromatography (CH$_2$Cl$_2$/MeOH 50:1) to give the title compound (378 mg, 18% yield).
$^1$H NMR (CDCl$_3$) δ 7.89 (d, 1H), 7.75 (m 1H), 7.59 (t, 1H), 7.48 (t, 1H), 4.92 (q, 1H), 3.00 (s, 3H), 1.45 (d, 3H).

b) 3-[(1S)-1-Chloroethyl]phenyl methyl sulfone

The title compound was obtained in 86% yield using general method F starting from (1R)-1-[3-(methylsulfonyl)phenyl]ethanol (370 mg, 1.85 mmol).
$^1$H NMR (CDCl$_3$) δ 7.95 (m, 1H), 7.87 (t, 1H), 7.69 (m, 1H), 7.55 (t, 1H), 5.10 (q, 1H), 3.04 (s, 3H), 1.83 (d, 3H).

c) (2R)-2-{[2-Amino-5-({(1R)-1-[3-(methylsulfonyl)phenyl]ethyl}thio)[1,3]thiazolo[4,5-d]pyrimidin-7-yl]amino}-4-methylpentan-1-ol The title compound was obtained in 34% yield using general method A starting from (2R)-2-[(2-amino-5-mercapto[1,3]thiazolo[4,5-d]pyrimidin-7-yl)amino]-4-methylpentan-1-ol (431 mg, 1.44 mmol) and 3-[(1S)-1-chloroethyl]phenyl methyl sulfone (350 mg, 1.44 mmol).
MS (ESI$^+$) m/z 482 [M+H]$^+$.

d) (2R)-2-{[2-Chloro-5-({(1R)-1-[3-(methylsulfonyl)phenyl]ethyl}thio)[1,3]thiazolo[4,5-d]pyrimidin-7-yl]amino}-4-methylpentan-1-ol The title compound was obtained in 92% yield using general method B starting from (2R)-2-{[2-amino-5-({(1R)-1-[3-(methylsulfonyl)phenyl]ethyl}thio)[1,3]thiazolo[4,5-d]pyrimidin-7-yl]amino}-4-methylpentan-1-ol (136 mg, 0.28 mmol).
MS (ESI$^+$) m/z 500 [M+H]$^+$.

e) (5R)-2-{[2-Methoxy-5-({(1R)-1-[3-(methylsulfonyl)phenyl]ethyl}thio)[1,3]-thiazolo[4,5-d]pyrimidin-7-yl]amino}-4-methylpentan-1-ol The title compound was obtained in 91% yield using general method C starting from (2R)-2-{[2-chloro-5-({(1R)-1-[3-(methylsulfonyl)phenyl]ethyl}thio)[1,3]thiazolo[4,5-d]pyrimidin-7-yl]amino}-4-methylpentan-1-ol (130 mg, 0.26 mmol).
MS (ESI$^+$) m/z 497 [M+H]$^+$.

f) 7-{[(1R)-1-(Hydroxymethyl)-3-methylbutyl]amino}-5-({(1R)-1-[3-(methylsulfonyl)phenyl]ethyl}thio)[1,3]thiazolo[4,5-d]pyrimidin-2(3H)-one The title compound was obtained in 19% yield using general method D starting from (2R)-2-{[2-methoxy-5-{(1R)-1-[3-(methylsulfonyl)phenyl]ethyl}thio)[1,3]-thiazolo[4,5-d]pyrimidin-7-yl]amino}-4-methylpentan-1-ol (118 mg, 0.24 mmol).
$^1$H NMR (CDCl$_3$) δ 8.18 (t, 1H), 7.77 (m, 2H), 7.51 (t, 1H), 5.00 (m, 1H), 4.91 (q, 1H), 4.19 (m, 1H), 3.80 (dd, 1H), 3.63 (dd, 1H), 3.08 (s, 3H), 1.71 (d, 3H), 1.63 (m, 1H), 1.46 (m, 2H), 0.94 (d, 3H), 0.87 (d, 3H);
MS (ESI$^+$) m/z 483 [M+H]$^+$.

EXAMPLE 2

7-{[(1R)-1-(Hydroxymethyl)-3-methylbutyl]amino}-5-({1-[3-(trifluoromethyl)phenyl]ethyl}thio)[1,3]thiazolo[4,5-d]pyrimidin-2(3H)-one a) (2R)-2-{2-Chloro-5-[2-chloro-7-((1R)-1-hydroxymethyl-3-methyl-butylamino)-thiazolo[4,5-d]pyrimidin-5-yldisulfanyl]-thiazolo[4,5-d]pyrimidin-7-ylamino}-4-methyl-pentan-1-ol Sodium nitrite (5.19 g, 75 mmol) in water (25 mL) was added dropwise at 0° C. to (2R)-2-[[2-amino-5-mercapto[1,3]thiazolo[4,5-d]pyrimidin-7-yl]amino]-4-methylpentan-1-ol (7.50 g, 25 mmol) in conc. HCl (150 mL) and CH$_3$CN (150 mL). The reaction mixture was stirred for 18 h at 0-5° C., and then poured onto ice (500 mL), and extracted with EtOAc. Any remaining solid was filtered off. The combined organic phases were washed sequentially with saturated NaCl solution and saturated aqueous NaHCO$_3$ solution. The organic phase was dried and evaporated and the solid previously filtered off was added to this. The total solid was slurried in EtOAc, which after filtration provided the title compound (6.3 g, 80% yield) as a solid.
$^1$H NMR (DMSO-d$_6$; integrals are for the monomeric unit) δ 7.98 (d, 1H), 4.47 (t, 1H), 3.99 (br s, 1H), 3.17 (m, 2H), 1.31-1.15 (m, 2H), 0.98 (m, 1H), 0.48 (d, 3H), 0.30 (d, 3H);
MS (ESI$^+$) m/z 635 [M+H]$^+$.

b) (2R)-2-{5-[7-((1R)-1-Hydroxymethyl-3-methyl-butylamino)-2-methoxy-thiazolo[4,5-d]pyrimidin-5-yldisulfanyl]-2-methoxy-thiazolo[4,5-d]pyrimidin-7-ylamino}-4-methyl-pentan-1-ol KOH (0.53 g, 9.4 mmol) in MeOH (5 mL) was added at 0° C. to a solution of (2R)-2-{2-chloro-5-[2-chloro-7-((1R)-1- hydroxymethyl-3-methyl-butylamino)-thiazolo[4,5-d]pyrimidin-5-yldisulfanyl]-thiazolo[4,5-d]pyrimidin-7-ylamino}-4-methyl-pentan-1-ol (3.0 g, 4.7 mmol) in MeOH (200 mL). The reaction was maintained at 0-5° C. for 18 h. The solvent was evaporated off and the residue taken up in MeOH/EtOAc (1:1). This solution was rapidly chromatographed (EtOAc) to provide the title compound (2.0 g, 68% yield).
MS (ESI⁺) m/z 627 [M+H]⁺.

c) 5-[7-{[(1R)-1-(Hydroxymethyl)-3-methylbutyl]amino}-[1,3]thiazolo[4,5-d]pyrimidin-2(3H)-one-5-yldisulfanyl]-7-{[(1R)-1-(hydroxymethyl)-3-methyl-butyl]amino}[1,3]thiazolo[4,5-d]pyrimidin-2(3H)-one A mixture of conc. HCl (20 mL) and water (20 mL) was added to a solution of (2R)-2-{5-[7-((1R)-1-hydroxymethyl-3-methyl-butylamino)-2-methoxy-thiazolo[4,5-d]pyrimidin-5-yldisulfanyl]-2-methoxy-thiazolo[4,5-d]pyrimidin-7-ylamino}-4-methyl-pentan-1-ol (1.5 g, 2.4 mmol) in 1,4-dioxane (20 mL). The solution was then stirred at 45° C. for 18 h. The solvent was evaporated off and the residue taken up in EtOAc (undissolved residue was filtered off and was found to be pure by LCMS). The solution was subjected to flash chromatography (MeOH:EtOAc 5:95). The two samples were pooled together to give the title compound (600 mg, 42% yield).
¹H NMR (DMSO-d₆; integrals are for the monomeric unit) δ 12.45 (s, 2H), 7.33 (d, 2H), 4.62 (t, 2H), 4.17 (br s, 2H), 1.48-1.31 (m, 4H), 1.25-1.14 (m, 2H), 0.72 (d, 6H), 0.56 (d, 6H);
MS (ESI⁺) m/z 599 [M+H]⁺.

d) 7-{[(1R)-1-(Hydroxymethyl)-3-methylbutyl]-amino}-5-({1-[3-(trifluoromethyl)phenyl]ethyl}thio)[1,3]thiazolo[4,5-d]pyrimidin-2(3H)-one The title compound was synthesized as a mixture of two diastereomers by general method G from the reaction of 5-[7-{[(1R)-1-(hydroxymethyl)-3-methylbutyl]amino}-[1,3]thiazolo[4,5-d]pyrimidin-2(3H)-one-5-yldisulfanyl]-7-{[(1R)-1-(hydroxymethyl)-3-methylbutyl]amino}[1,3]thiazolo[4,5-d]pyrimidin-2(3H)-one (20 mg, 0.033 mmol) and 3-(1-bromoethyl)trifluoromethylbenzene (11 μL, 0.066 mmol) to give 10 mg (31% yield). ¹H NMR (CDCl₃) δ 7.68 (m, 2H) 7.51 (m, 1H) 7.42 (m, 1H) 4.97 (q, 1H) 4.91 (m, 1H) 4.38-4.27 (m, 0.5H) 4.26-4.16 (m, 0.5H) 3.85 (dd, 0.5H) 3.64 (m, 1H) 3.53 (dd, 0.5H) 1.71 (dd, 3H) 1.64 (m, 1H) 1.57-1.46 (m, 1H) 1.45-1.34 (m, 1H) 0.96 (dd, 3H) 0.88 (dd, 3H);
MS (ESI⁺) m/z 473 [M+H]⁺.

EXAMPLE 3

7-{[(1R)-1-(Hydroxymethyl)butyl]amino}-5-{[(1S)-1-phenylethyl]thio}[1,3]thiazolo[4,5-d]pyrimidin-2(3H)-one a) (2R)-2-{[2-Amino-5-(benzylthio)[1,3]thiazolo[4,5-d]pyrimidin-7-yl]amino}pentan-1-ol 5-(Benzylthio)-7-chloro[1,3]thiazolo[4,5-d]pyrimidin-2-amine (6.0 g, 19.4 mmol) was dissolved in NMP (30 mL). DIPEA (8.4 mL, 48.5 mmol) and 2-amino-(2R)-1-pentanol (3.5 g, 33.9 mmol) were added and the mixture was heated to 110° C. for 4 days. After cooling to room temperature, the mixture was poured into water (200 mL). The precipitated product was collected by filtration, washed with water and used in the next step without further purification (7.0 g, 97% yield).
MS (ESI⁺) m/z 376 [M+H]⁺.

b) (2R)-2-[(2-Amino-5-mercapto[1,3]thiazolo[4,5-d]pyrimidin-7-yl)amino]pentan-1-ol A round-bottomed flask was equipped with a dry ice-ethanol condenser and immersed in a dry ice-ethanol cooling bath. Ammonia (250 mL) was condensed into the flask followed by addition of (2R)-2-{[2-amino-5-(benzylthio)[1,3]thiazolo[4,5-d]pyrimidin-7-yl]amino}pentan-1-ol (6.8 g, 18.1 mmol). The resulting mixture was allowed to warm to −33° C. and sodium metal was added in small pieces until a blue colour appeared and persisted for 30 seconds. The reaction was then quenched by addition of a spoonful of solid ammonium chloride. The ammonia was evaporated off and water (250 mL) was added to the residue. The resulting mixture was neutralized with 1M HCl (aq). The precipitated product was collected by filtration, washed with water and dried in vacuo to yield 4.15 g (80% yield) of the title compound.
MS (ESI⁺) m/z 286 [M+H]⁺.

c) (2R)-2-{2-Chloro-5-[2-chloro-7-((1R)-1-hydroxymethylbutylamino)-thiazolo[4,5-d]pyrimidin-5-yldisuyfanyl]-thiazolo[4,5-d]pyrimidin-7-ylamino}-pentan-1-ol Following the procedure of Example 2(a) gave the title compound in 78% yield starting from (2R)-2-[(2-amino-5-mercapto[1,3]thiazolo[4,5-d]pyrimidin-7-yl)amino]pentan-1-ol is (4.0 g, 14 mmol), sodium nitrite (1.93 g, 28 mmol), HCl (100 mL), CH₃CN (100 ml) and H₂0 (10 mL).
¹H NMR (DMSO-d₆) δ 8.27 (d, 1H), 4.32-3.81 (m, 2H), 3.50-3.23 (m, 2H), 1.37-1.19 (m, 2H), 1.10-0.93 (m, 1H), 0.94-0.78 (m, 1H), 0.49 (t, 3H);
MS (ESI⁺) m/z 607 [M+H]⁺.

d) (2R)-2-{5-[7-((1R)-1-Hydroxymethylbutylamino)-2-methoxy-thiazolo[4,5-d]pyrimidin-5-yldisulfanyl]-2-methoxy-thiazolo[4,5-d]pyrimidin-7-ylamino}-pentan-1-ol KOH (495 mg, 8.8 mmol) was added to (2R)-2-{2-chloro-5-[2-chloro-7-((1R)-1-hydroxymethylbutylamino)-thiazolo[4,5-d]pyrimidin-5-yldisulfanyl]-thiazolo[4,5-d]pyrimidin-7-ylamino}-pentan-1-ol (2.68 g, 4.41 mmol) in MeOH (200 mL) at 0° C. The reaction was stirred at 0° C. overnight and then the methanol was evaporated off. The residue was poured into water and the resulting precipitate was collected by filtration. The crude wet product was used in the next step without any further purification.
MS (ESI⁺) m/z 599 [M+H]⁺.

e) 5-[7-{[(1R)-1-(Hydroxymethyl)]-amino}-[1,3]thiazolo[4,5-d]pyrimidin-2(3H)-one-5-yldisulfanyl]-7-{[(1R)-1-(hydroxymethylbutyl]amino}[1,3]thiazolo[4,5-d]pyrimidin-2(3H)-one Following the procedure of Example 2(c) gave the title compound in 59% yield (over two steps) starting from crude (2R)-2-{5-[7-((1R)-1-hydroxymethylbutylamino)-2-methoxy-thiazolo[4,5-d]-pyrimidin-5-yldisulfanyl]-2-methoxy-thiazolo[4,5-d]pyrimidin-7-ylamino}-pentan-1-ol (4.41 mmol) (Example 3(d)), conc. HCl (2 mL), water (2 mL) and 1,4-dioxane (100 mL).

$^1$H NMR (DMSO-d$_6$) δ 12.46 (s, 1H), 7.33 (d, 1H), 4.61 (t, 1H), 4.10 (br. s., 1H), 3.35 (t, 2H), 1.37-1.20 (m, 2H), 1.13-1.10 (m, 1H), 0.96-0.82 (m, 1H), 0.59 (t, 3H)
MS (ESI$^+$) m/z 571 [M+H]$^+$.

f) [(1R)-1-Chloroethyl]benzene

The title compound was obtained in 67% yield using general method F and starting from (1S)-1-phenylethanol (25 g, 0.20 mol).
$^1$H NMR (CDCl$_3$) δ 7.42 (m, 2H), 7.36 (m, 2H), 7.30 (m, 1H), 5.09 (q, 1H), 1.85 (d, 3H);
MS (CI) m/z 141 [M+1].

g) 7-{[(1R)-1-(hydroxymethyl)butyl]amino}-5-{[(1S)-1-phenylethyl]thio}[1,3]thiazolo[4,5-d]pyrimidin-2(3H)-one 7-{[(1R)-1-(Hydroxymethyl)butyl]amino}-5-{[(1S)-1-phenylethyl]thio}[1,3]thiazolo[4,5-d]pyrimidin-2(3H)-one was prepared in 22% yield from 5,5'-dithiobis[7-{[(1R)-1-(hydroxymethyl)butyl]amino}[1,3]thiazolo[4,5-d]pyrimidin-2(3H)-one] (40 mg, 0.07 mmol) and [(1R)-1-chloroethyl]benzene (29 mg, 0.21 mmol) using general method G.
$^1$H NMR (DMSO-d$_6$) δ 12.34 (br s, 1H) 7.44 (d, 2H) 7.33 (m, 2H) 7.23 (m, 2H) 4.93 (q, 1H) 4.68 (t, 1H) 4.21 (br s, 1H) 3.49-3.33 (m, 2H) 1.68 (d, 3H) 1.64-1.51 (m, 1H) 1.50-1.39 (m, 1H) 1.34 (m, 2H) 0.87 (t, 3H);
MS (ESI$^+$) m/z 391 [M+H]$^+$.

EXAMPLE 4

7-{[(1R)-1-(Hydroxymethyl)-3-methylbutyl]amino}-5-({(1S)-1-[3-(methylsulfonyl)phenyl]ethyl}thio)[1,3]thiazolo[4,5-d]pyrimidin-2(3H)-one a) (1S)-1-[3-(Methylsulfonyl)phenyl]ethanol The title compound was prepared in 58% yield from 1-[3-(methylsulfonyl)phenyl]ethanone (2.00 g, 10.1 mmol) using general method E.
MS (ESI$^+$) m/z 201 [M+H]$^+$.

b) 1-[(1R)-1-Chloroethyl]-3-(methylsulfonyl)benzene

The title compound was prepared in 21% yield from (1S)-1-[3-(methylsulfonyl)phenyl]ethanol (100 mg, 0.50 mmol) using general method F.
MS (ESI$^+$) m/z 219 [M+H]$^+$.

c) (2R)-2-{[2-Amino-5-({(1S)-1-[3-(methylsulfonyl)phenyl]ethyl}thio)[1,3]thiazolo[4,5-d]pyrimidin-7-yl]-amino}-4-methylpentan-1-ol The title compound was prepared from (2R)-2-[(2-amino-5-mercapto[1,3]thiazolo[4,5-d]pyrimidin-7-yl)amino]-4-methylpentan-1-ol (16.5 g, 55.3 mmol) and 1-[(1R)-1-chloroethyl]-3-(methylsulfonyl)benzene (12.1 g, 55.3 mmol) using general method A.
$^1$H NMR (600 MHz, DMSO-d$_6$) 8.00 (m, 3H) 7.81 (m, 2H) 7.60 (t, 1H) 6.91 (d, 1H) 5.06 (q, 1H) 4.66 (t, 1H) 4.24 (br s, 1H) 3.38 (m, 1H) 3.28 (m, 1H) 3.23 (s, 3H) 1.69 (d, 3H) 1.59 (m, 1H) 1.46-1.34 (m, 2H) 0.86 (m, 6H);
MS (ESI$^+$) m/z 482 [M+H]$^+$.

d) (2R)-2-[{2-Chloro-5-({(1S)-1-[3-(methylsulfonyl)phenyl]ethyl}thio)[1,3]thiazolo[4,5-d]pyrimidin-7-yl]amino}-4-methylpentan-1-ol The title compound was prepared from (2R)-2-{[2-amino-5-({(1S)-1-[3-(methylsulfonyl)phenyl]ethyl}thio)[1,3]thiazolo[4,5-d]pyrimidin-7-yl]amino}-4-methylpentan-1-ol using general method B.
MS (ESI$^+$) m/z 501 [M+H]$^+$.

e) (2R)-2-{[2-Methoxy-5-({(1S)-1-[3-(methylsulfonyl)phenyl]ethyl}thio)[1,3]thiazolo[4,5-d]pyrimidin-7-yl]amino}-4-methylpentan-1-ol The title compound was prepared from (2R)-2-{[2-chloro-5-({(1S)-1-[3-(methylsulfonyl)phenyl]ethyl}thio)[1,3]thiazolo[4,5-d]pyrimidin-7-yl]amino}-4-methylpentan-1-ol using general method C.
MS (ESI$^+$) m/z 497 [M+H]$^+$.

f) 7-{[(1R)-1-(Hydroxymethyl)-3-methylbutyl]amino}-5-({(1S)-1-[3-(methylsulfonyl)phenyl]ethyl}thio)[1,3]thiazolo[4,5-d]pyrimidin-2(3H)-one The title compound was prepared from (2R)-2-{[2-methoxy-5-({(1S)-1-[3-(methylsulfonyl)phenyl]ethyl}thio)[1,3]thiazolo[4,5-d]pyrimidin-7-yl]amino}-4-methylpentan-1-ol using general method D. Overall yield 490 mg, 38% over three steps. $^1$H NMR (CDCl$_3$) δ 8.07 (m, 1H) 7.78 (m, 2H) 7.52 (m, 1H) 4.95 (q, 1H) 4.63 (m, 1H) 4.34 (br s, 1H) 3.73 (m, 1H) 3.57 (m, 1H) 3.07 (s, 3H) 1.70 (d, 3H) 1.64 (m, 1H) 1.48-1.38 (m, 2H) 0.93 (m, 6H);
MS (ESI$^+$) m/z 483 [M+H]$^+$.

EXAMPLE 5

7-{[(1R)-1-(Hydroxymethyl)-3-methylbutyl]amino}-5-({1-[3-(trifluoromethyl)phenyl]ethyl}thio)[1,3]thiazolo[4,5-d]pyrimidin-2(3H)-one Separation of the diastereomeric mixture produced in Example 2 by preparative HPLC gave a single diastereomer (5 mg, 15% yield).
$^1$H NMR (CDCl$_3$) δ 7.69 (s, 1H) 7.66 (d, 1H) 7.50 (m, 1H) 7.42 (t, 1H) 4.97 (q, 1H) 4.77 (d, 1H) 4.25-4.15 (m, 1H) 3.84 (dd, 1H) 3.64 (dd, 1H) 1.72 (d, 3H) 1.67-1.57 (m, 1H) 1.57-1.47 (m, 1H) 1.44-1.34 (m, 1H) 0.87 (dd, 6H);
MS (ESI$^+$) m/z 473 [M+H]$^+$.

EXAMPLE 6

7-{[(1R)-1-(Hydroxymethyl)-3-methylbutyl]amino}-5-({1-[2-(trifluoromethyl)phenyl]ethyl}thio)[1,3]thiazolo[4,5-d]pyrimidin-2(3H)-one)

The title compound was synthesized as a mixture of two diastereomers by general method G from the reaction of 5-[7-{[(1R)-1-(hydroxymethyl)-3-methylbutyl]amino}-[1,3]thiazolo[4,5-d]pyrimidin-2(3H)-one-5-yldisulfanyl]-7-{[(1R)-1-(hydroxymethyl)-3-methylbutyl]amino}[1,3]thiazolo[4,5-d]pyrimidin-2(3H)-one (20 mg, 0.033 mmol) and 2-(1-bromoethyl)trifluoromethylbenzene (11 μL, 0.066 mmol) to give 13 mg (43% yield). $^1$H NMR (CDCl$_3$) δ 7.69 (d, 1H) 7.63 (m, 1H) 7.53 (q, 1H) 7.34 (m, 1H) 5.45 (q, 0.5H) 5.39 (q, 0.5H) 5.21 (t, 1H) 4.46 (d, 1H) 3.86 (m, 1H) 3.68 (m, 1H) 1.73 (d, 3H) 1.69 (m, 1H) 1.65-1.55 (m, 1H) 1.47 (m, 1H) 0.98-0.88 (m, 6H);
MS (ESI$^+$) m/z 473 [M+H]$^+$.

EXAMPLE 7

7-{[(1R)-1-(Hydroxymethyl)-3-methylbutyl]amino}-5-({1-[2-(trifluoromethyl)phenyl]ethyl}thio)[1,3]thiazolo[4,5-d]pyrimidin-2(3H)-one Separation of the diastereomeric mixture produced in Example 6 by preparative HPLC gave a single diastereomer (4 mg, 13% yield).

$^1$H NMR (CDCl$_3$) δ 7.71 (d, 3H) 7.65 (d, 1H) 7.55 (t, 1H) 7.36 (t, 1H) 5.40 (q, 1H) 4.71 (d, 1H) 4.42 (m, 1H) 3.83 (dd, 1H) 3.68 (dd, 1H) 1.76 (d, 3H) 1.74-1.64 (m, 1H) 1.64-1.53 (m, 1H) 1.54-1.43 (m, 1H) 0.96 (dd, 6H);

MS (ESI$^+$) m/z 473 [M+H]$^+$.

EXAMPLE 8

7-{[(1R)-1-(Hydroxymethyl)butyl]amino}-5-({(1S)-1-[3-(methylsulfonyl)phenyl]ethyl}thio)[1,3]thiazolo[4,5-d]pyrimidin-2(3H)-one The title compound was obtained in 55% yield using general method G starting from 5-[7-{[(1R)-1-(hydroxymethyl)]amino}-[1,3]thiazolo[4,5-d]pyrimidin-2(3H)-one-5-yldisulfanyl]-7-{[(1R)-1-(hydroxymethylbutyl]amino}[1,3]thiazolo[4,5-d]pyrimidin-2(3H)-one (55 mg, 0.087 mmol) and 1-[(1R)-1-chloroethyl]-3-(methylsulfonyl)benzene (38 mg, 0.17 mmol).

$^1$H NMR (CDCl$_3$) δ 10.64 (br s, 13H), 8.03 (s, 1H), 7.78 (m, 2H), 7.50 (t, 1H), 5.52 (d, 1H), 4.96 (q, 1H), 4.23 (m, 1H), 3.79 (m, 1H), 3.64 (m, 1H), 3.08 (s, 3H), 1.67 (d, 3H), 1.55 (m, 1H), 1.38 (m, 1H), 0.89 (m, 5H);

MS (ESI$^+$) m/z 469 [M+H]$^+$.

EXAMPLE 9

7-{[(1R)-1-(Hydroxymethyl)-3-methylbutyl]amino}-5-[(1-phenylethyl)thio]-[1,3]thiazolo[4,5-d]pyrimidin-2(3H)-one a) (2R)-2-({2-Amino-5-[(1-phenylethyl)thio][1,3]thiazolo[4,5-d]pyrimidin-7-yl}amino)-4-methylpentan-1-ol The title compound was obtained in 67% yield according to general method A starting from (2R)-2-[(2-amino-5-mercapto[1,3]thiazolo[4,5-d]pyrimidin-7-yl)amino]-4-methylpentan-1-ol (320 mg, 1.01 mmol) and (1-bromoethyl)-benzene (245 mg, 1.21 mmol).

$^1$H NMR (DMSO-d$_6$) δ 7.94 (s, 2H), 7.16 (m, 2H), 7.14 (m, 2H), 6.97 (m, 1H), 6.77 (d, 1H), 4.74 (m, 1H), 4.49 (m, 1H), 4.03 (m, 1H), 3.87 (m, 2H), 3.22 (m, 2H), 1.72 (dd, 1H), 1.61 (m, 1H), 1.42 (m, 2H), 0.87 (d, 3H), 0.85 (dd, 3H);

MS (ESI$^+$) m/z 405 [M+H]$^+$.

b) (2R)-2-({2-Chloro-5-[(1-phenylethyl)thio][1,3]thiazolo[4,5-d]pyrimidin-7-yl}amino)-4-methylpentan-1-ol The title compound was obtained in 71% yield according to general method B starting from (2R)-2-({2-amino-5-[(1-phenylethyl)thio][1,3]thiazolo[4,5-d]pyrimidin-7-yl}amino)-4-methylpentan-1-ol (335 mg, 0.83 mmol);

MS (ESI$^+$) m/z 423/425 [M+H]$^+$.

c) (2R)-2-({2-Methoxy-5-[(1-phenylethyl)thio][1,3]thiazolo[4,5-d]pyrimidin-7-yl}amino)-4-methylpentan-1-ol The title compound was obtained in 70% yield according to general method C starting from (2R)-2-({2-chloro-5-[(1-phenylethyl)thio][1,3]thiazolo[4,5-d]pyrimidin-7-yl}amino)-4-methylpentan-1-ol (500 mg, 1.2 mmol);

MS (ESI$^+$) m/z 419 [M+H]$^+$.

d) 7-{[(1R)-1-(Hydroxymethyl)-3-methylbutyl]amino}-5-[(1-phenylethyl)thio][1,3]thiazolo[4,5-d]pyrimidin-2(3H)-one The title compound was obtained as a mixture of two diastereomers in 68% yield according to method D starting from (2R)-2-({2-methoxy-5-[(1-phenylethyl)thio][1,3]thiazolo[4,5-d]pyrimidin-7-yl}amino)-4-methylpentan-1-ol (320 mg, 0.76 mmol).

$^1$H NMR (DMSO-d$_6$) 7.43 (m, 2H), 7.41 (m, 2H), 7.31 (m, 1H), 6.37 (br s, 1H), 4.94 (m, 1H), 4.64 (m, 1H), 4.25 (m, 1H), 3.45-3.39 (m, 2H), 3.38-3.27 (m, 2H), 1.66 (d, 3H), 1.60 (m, 1H), 1.42 (m, 1H), 0.89 (d, 3H), 0.85 (d, 3H);

MS (ESI$^+$) m/z 405 [M+H]$^+$.

EXAMPLE 10

7-{[(1R)-1-(Hydroxymethyl)-3-methylbutyl]amino}-5-{[(1R)-1-phenylethyl]thio}[1,3]thiazolo[4,5-d]pyrimidin-2(3H)-one a) (2R)-2-[2-Amino-5-{[1R)-1-phenylethyl]thio}[1,3]thiazolo[4,5-d]pyrimidin-7-yl)amino]-4-methylpentan-1-ol HPLC purification of (2R)-2-({2-amino-5-[(1-phenylethyl)thio][1,3]thiazolo[4,5-d]pyrimidin-7-yl}amino)-4-methylpentan-1-ol (Example 9(a), 500 mg) provided the title compound (150 mg) as a single diastereomer.

$^1$H NMR (DMSO-d$_6$) 7.98 (s, 2H), 7.45 (m, 2H), 7.32 (m, 2H), 7.24 (m, 1H), 6.87 (d, 1H), 4.95 (q, 1H), 4.24 (br s, 1H), 3.45 (m, 1H), 3.35 (m, 1H), 1.68 (d, 3H), 1.62 (m, 1H), 1.42 (m, 2H), 0.88 (d, 3H), 0.82 (d, 3H).

b) (2R)-2-[(2-Chloro-5-{[(1R)-1-phenylethyl]thio}[1,3]thiazolo[4,5-d]pyrimidin-7-yl)amino]-4-methylpentan-1-ol The title compound was obtained in 51% yield using method B and starting from (2R)-2-[(2-amino-5-{[(1R)-1-phenylethyl]thio}[1,3]thiazolo[4,5-d]pyrimidin-7-yl)amino]-4-methylpentan-1-ol (150 mg, 0.37 mmol).

MS (ESI$^+$) m/z 423/425 [M+H]$^+$.

c) (2R)-2-[(2-Methoxy-5-{[(1R)-1-phenylethyl]thio}[1,3]thiazolo[4,5-d]pyrimidin-7-yl)amino]-4-methylpentan-1-ol The title compound was obtained in 91% yield using method C and starting from (2R)-2-[(2-chloro-5-{[(1R)-1-phenylethyl]thio}[1,3]thiazolo[4,5-d]pyrimidin-7-yl)amino]-4-methylpentan-1-ol (70 mg, 0.17 mmol).

MS (ESI$^+$) m/z 419 [M+H]$^+$.

d) 7-{[(1R)-1-(Hydroxymethyl)-3-methylbutyl] amino}-5-{[1R)-1-phenylethyl]thio}[1,3]thiazolo[4,5-d]pyrimidin-2(3H)-one The title compound was obtained in 67% yield according to method D and starting from (2R)-2-[(2-methoxy-5-{[(1R)-1-phenylethyl]thio}[1,3]thiazolo[4,5-d]pyrimidin-7-yl) amino]-4-methylpentan-1-ol (65 mg, 0.15 mmol).

$^1$H NMR (DMSO-d$_6$) 12.36 (s, 1H), 7.42 (m, 2H), 7.33 (m, 2H), 4.91 (q, 1H), 4.72 (m, 1H), 4.25 (br s, 1H), 3.44 (m, 1H), 3.37 (m, 1H), 1.69 (d, 3H), 1.58 (d, 1H), 1.38 (m, 2H), 0.88 (d, 3H), 0.84 (d, 3H);

MS (ESI$^+$) m/z 405 [M+H]$^+$.

EXAMPLE 11

7-{[(1R)-1-(Hydroxymethyl)-3-methylbutyl]amino}-5-{[(1S)-1-phenylethyl]thio}[1,3]thiazolo[4,5-d]pyrimidin-2(3H)-one a) (2R)-2-[(2-Amino-5-{[(1S)-1-phenylethyl]thio}[1,3]thiazolo[4,5-d]pyrimidin-7-yl)amino]-4-methyl-pentan-1-ol The title compound was obtained in 42% yield using general method A and starting from (2R)-2-[(2-amino-5-mercapto[1,3]thiazolo[4,5-d]pyrimidin-7-yl)amino]-4-methylpentan-1-ol (27 g, 90 mmol) and [(1R)-1-chloroethyl] benzene (19 g, 135 mmol).

$^1$H NMR (DMSO-d$_6$) δ 7.95 (br s, 2H), 7.43 (m, 2H), 7.31 (m, 2H), 7.22 (m, 1H), 6.85 (d, 1H), 4.96 (q, 1H), 4.64 (t, 1H), 4.27 (br s, 1H), 3.44-3.30 (m, 2H), 1.66 (d, 3H), 1.59 (m, 1H), 1.41 (m, 2H), 0.87 (d, 3H), 0.84 (d, 3H);

MS (ESI$^+$) m/z 404 [M+H]$^+$.

b) (2R)-2-[(2-Chloro-5-{[(1S)-1-phenylethyl]thio}[1,3]thiazolo[4,5-d]pyrimidin-7-yl)amino]-4-methyl-pentan-1-ol The title compound was obtained in 85% yield according to general method B and starting from (2R)-2-[(2-amino-5-{[(1S)-1-phenylethyl]thio}[1,3]thiazolo[4,5-d]pyrimidin-7-yl)amino]-4-methylpentan-1-ol (70 mg, 0.17 mmol).

MS (ESI$^+$) m/z 423/425 [M+H]$^+$.

c) (2R)-2-[(2-Methoxy-5-{[(1S)-1-phenylethyl]thio}[1,3]thiazolo[4,5-d]pyrimidin-7-yl)amino]-4-methyl-pentan-1-ol The title compound was obtained in 51% yield according to general method C and starting from (2R)-2-[(2-chloro-5-{[(1S)-1-phenylethyl]thio}[1,3]thiazolo[4,5-d]pyrimidin-7-yl)amino]-4-methylpentan-1-ol (77 mg, 0.18 mmol).

MS (ESI$^+$) m/z 419 [M+H]$^+$.

d) 7-{[(1R)-1-(Hydroxymethyl)-3-methylbutyl]-amino}-5-{[(1S)-1-phenylethyl]thio}[1,3]thiazolo[4,5-d]pyrimidin-2(3H)-one The title compound was obtained in 37% yield according to general method D and starting from (2R)-2-[(2-methoxy-5-{[(1S)-1-phenylethyl]thio}[1,3]thiazolo[4,5-d]pyrimidin-7-yl)amino]-4-methylpentan-1-ol (50 mg, 0.12 mmol).

$^1$H NMR (DMSO-d$_6$) δ 7.36 (m, 2H), 7.25 (m, 2H), 7.17 (m, 1H), 7.05 (br s, 1H), 4.87 (m, 1H), 4.62 (m, 1H), 4.24 (m, 1H), 3.35 (m, 2H), 3.25 (m, 2H), 1.62 (m, 2H), 1.55 (d, 1H), 1.35 (m, 1H), 0.84 (d, 3H), 0.78 (d, 3H);

MS (ESI$^+$) m/z 405 [M+H]$^+$.

EXAMPLE 12

3-{(1S)-1-[(7-{[(1R)-1-(Hydroxymethyl)butyl]amino}-2-oxo-2,3-dihydro[1,3]thiazolo[4,5-d]pyrimidin-5-yl)thio]ethyl}benzonitrile a) 3-[(1R)-1-Chloroethyl]-benzonitrile

The title compound was obtained in 79% yield according to general method F and starting from 3-[(1S)-1-hydroxyethyl] benzonitrile (3.35 g, 22.8 mmol).

$^1$H NMR (DMSO-d$_6$): δ 7.97 (s, 1H), 7.82 (m, 2H), 7.60 (t, 1H), 5.40 (q, 1H), 1.80 (d, 3H); $^{13}$C NMR (DMSO-d$_6$): δ144.1, 131.2, 131.6, 130.3, 129.9, 118.4, 111.6, 57.41, 25.5;

MS (ESI$^+$) m/z 166 [M+H]$^+$, b) 3-{(1S)-1-[(2-Amino-7-{[(1R)-1-(hydroxymethyl) butyl]amino}[1,3]thiazolo[4,5-d]pyrimidin-5-yl)thio] ethyl}benzonitrile The title compound was obtained in 75% yield according to general method A and starting from 2-amino-7-{[(1R)-1-(hydroxymethyl)butyl]amino}[1,3]thiazolo[4,5-d]pyrimidine-5(6H)-thione (2.87 g, 10.0 mmol) and 3-[(1R)-1-chloroethyl]benzonitrile (2.31 g, 13.9 mmol).

$^1$H NMR (DMSO-d$_6$): δ 8.00 (s, 2H), 7.91 (s, 1H), 7.82 (m, 1H), 7.69 (m, 1H), 7.52 (t, 1H), 6.90 (d, 1H), 5.00 (q, 1H), 4.63 (t, 1H), 4.13 (br s, 1H), 3.41 (m, 1H), 3.30 (m, 1H), 1.66 (d, 3H), 1.57 (m, 1H), 1.43 (m, 1H), 1.29 (m, 2H), 0.86 (t, 3H);

$^{13}$C NMR (DMSO-d$_6$): δ 170.8, 168.7, 165.1, 155.7, 145.9, 132.3, 130.8, 130.6, 129.5, 118.7, 111.2, 63.3, 59.7, 51.8, 42.3, 33.0, 21.8, 18.8, 14.0;

MS (ESI$^+$) m/z 415 [M+H]$^+$.

c) 3-{(1S)-1-[(2-Chloro-7-{[(1R)-1-(hydroxymethyl) butyl]amino}[1,3]thiazolo[4,5-d]pyrimidin-5-yl)thio] ethyl}benzonitrile The title compound was obtained in 84% yield according to general method B and starting from 3-{(1S)-1-[(2-amino-7-{[(1R)-1-(hydroxymethyl)butyl]amino}[1,3]thiazolo[4,5-d]pyrimidin-5-yl)thio]ethyl}benzonitrile (3.09 g, 7.46 mmol).

hu 1H NMR (DMSO-d$_6$): δ 8.19 (d, 1H), 7.95 (br s, 1H), 7.85 (d, 1H), 7.71 (d, 1H), 7.54 (t, 1H), 5.05 (q, 1H), 4.21 (m, 1H), 3.45-3.34 (m, 2H), 1.69 (d, 3H), 1.60 (m, 1H), 1.48 (m, 1H), 1.37-1.22 (m, 2H), 0.86 (t, 3H);

MS (ESI$^+$) m/z 434 [M+H]$^+$.

d) 3-{(1S)-1-[(7-{[(1R)-1-(Hydroxymethyl)butyl] amino}-2-methoxy[1,3]thiazolo[4,5-d]pyrimidin-5-yl)thio]ethyl}benzonitrile The title compound was produced according to general method C and starting from 3-{(1S)-1-[(2-chloro-7-{[(1R)-1-(hydroxymethyl)butyl]amino}-[1,3]thiazolo[4,5-d]pyrimidin-5-yl)thio]ethyl}benzonitrile (2.43 g, 5.61 mmol).

$^1$H NMR (DMSO-d$_6$): δ 7.94 (br s, 1H), 7.83 (m, 1H), 7.71 (m, 1H), 7.54 (m, 2H), 5.04 (q, 1H), 4.68 (m, 1H), 4.18 (br s, 1H), 4.16 (s, 3H), 3.44-3.30 (m, 2H), 1.69 (d, 3H), 1.63-1.54 (m, 1H), 1.45 (m, 1H), 1.35-1.23 (m, 2H), 0.86 (t, 3H);

MS (ESI$^+$) m/z 430 [M+H]$^+$.

e) 3-{(1S)-1-[(7-{[(1R)-1-(Hydroxymethyl)butyl] amino}-2-oxo-2,3-dihydro[1,3]thiazolo[4,5-d]pyrimidin-5-yl)thio]ethyl}benzonitrile The title compound was obtained in 19% yield according to general method D starting from 3-{(1S)-1-[(7-{[(1R)-1-(hydroxymethyl)butyl]amino}-2-methoxy[1,3]thiazolo[4,5-d]pyrimidin-5-yl)thio]ethyl}benzonitrile.

$^1$H NMR (DMSO-d$_6$): δ 12.39 (s, 1H), 7.93 (s, 1H), 7.84 (d, 1H), 7.70 (d, 1H), 7.53 (t, 1H), 7.24 (d, 1H), 4.95 (q, 1H), 4.66 (m, 1H), 4.15 (br s, 1H), 3.42-3.27 (m, 2H), 1.67 (d, 3H), 1.57 (m, 1H), 1.43 (m, 1H), 1.35-1.22 (m, 2H), 0.86 (t, 3H);

$^{13}$C NMR (DMSO-d$_6$): δ 171.9, 169.2, 165.8, 154.9, 145.4, 132.3, 130.8, 130.8, 129.6, 118.7, 111.4, 91.0, 63.1, 59.7, 42.6, 32.8, 21.0, 18.8, 13.8;

MS (ESI$^+$) m/z 416 [M+H]$^+$.

EXAMPLE 13

7-{[(1R)-1-(Hydroxymethyl)-3-methylbutyl]amino}-5-({1-[3-(methylsulfonyl)phenyl]ethyl}thio)[1,3]thiazolo[4,5-d]pyrimidin-2(3H)-one a) 1-[3-(Methylsulfonyl)phenyl]ethanol

Methylmagnesium iodide (3M in THF, 13.2 mL, 4.4 mmol) was added dropwise via syringe at 0° C. to 3-(methylsulfonyl)benzaldehyde (0.74 g, 4.0 mmol) in THF (15 mL). The resulting reaction mixture was stirred at 0° C. until no more conversion to product occurred (monitored by GC-MS). The reaction was quenched with saturated ammonium chloride, the aqueous phase was extracted with EtOAc and the organic phase was washed with saturated sodium bicarbonate, brine, dried (MgSO$_4$), filtered and concentrated in vacuo. The crude product was purified by flash column chromatography on silica (EtOAc:hexane 1:4) to give the title compound (260 mg) that was used in the next step without any further purification (approximate purity 50%).

GC-MS (EI) (HP5MS, 0.25 mm×30 m, 0.25 μm) m/z 200 M$^+$.

b) 1-(1-Chloroethyl)-3-(methylsulfonyl)benzene

Thionyl chloride (0.11 g, 0.91 mmol) was added to a solution of N,N-diethylaniline (0.19 g, 1.3 mmol) and 1-[3-(methylsulfonyl)phenyl]ethanol (0.26 g, 1.3 mmol) in toluene (4 mL) at 0° C. The reaction mixture was stirred at 0° C. for 30 minutes followed by addition of EtOAc. The organic phase was washed subsequently with 2M HCl (aq), water, saturated sodium bicarbonate, and brine, and then dried (MgSO$_4$), filtered and concentrated in vacuo. The crude product was purified by flash column chromatography on silica (ethyl acetate: hexane gradient elution 20:80 to 25:75) to give the title compound (60 mg) that was used in the next step without any further purification (approximate purity 75%).

GC-MS (EI) (HP5MS, 0.25 mm×30 m, 0.25 μm) m/z 218 M$^+$.

c) 7-{[(1R)-1-(Hydroxymethyl)-3-methylbutyl]amino}-5-({1-[3-(methylsulfonyl)phenyl]ethyl}thio)[1,3]thiazolo[4,5-d]pyrimidin-2(3H)-one The title compound was obtained as a mixture of two diastereomers in 42% yield starting from 1-(1-chloroethyl)-3-(methylsulfonyl)benzene (27 mg, 0.12 mmol) and 5-[7-{[(1R)-1-(hydroxymethyl)-3-methylbutyl]amino}-[1,3]thiazolo[4,5-d]pyrimidin-2(3H)-one-5-yldisulfanyl]-7-{[(1R)-1-(hydroxymethyl)-3-methylbutyl]amino}[1,3]thiazolo[4,5-d]pyrimidin-2(3H)-one (30 mg, 0.05 mmol) using the general method G but with the following modifications: sodium borohydride (3 equiv.) was added and the reaction was stirred at room temperature.

$^1$H NMR (MeOH-d$_4$) δ 8.06 (m, 1H), 7.84 (m, 2H), 7.58 (m, 1H), 5.12 (m, 1H), 4.41 (m, 0.5H from one diastereomer), 4.36-4.25 (m, 0.5H from one diastereomer), 3.57-3.42 (m, 2H), 3.12 (s, 1.5H from one diastereomer), 3.11 (s, 1.5H from one diastereomer), 1.74 (d, 1.5H from one diastereomer), 1.72 (d, 1.5H from one diastereomer), 1.70-1.56 (m, 1H), 1.56-1.36 (m, 2H), 0.93 (m, 6H);

MS (ESI$^+$) m/z 483 [M+H]$^+$.

EXAMPLE 14

3-{1-[(7-{[(1R)-1-(Hydroxymethyl)-3-methylbutyl]amino}-2-oxo-2,3-dihydro[1,3]thiazolo[4,5-d]pyrimidin-5-yl)thio]ethyl}benzamide 3-{(1S)-1-[(7-{[(1R)-1-(Hydroxymethyl)-3-methylbutyl]amino}-2-oxo-2,3-dihydro[1,3]thiazolo[4,5-d]pyrimidin-5-yl)thio]ethyl}benzamide;

and

3-{(1R)-1-[(7-{[(1R)-1-(Hydroxymethyl)-3-methylbutyl]amino}-2-oxo-2,3-dihydro[1,3]thiazolo[4,5-d]pyrimidin-5-yl)thio]ethyl}benzamide a) 3-(1-Chloroethyl)benzamide

Diethylaniline (390 μL, 2.45 mmol) was added 3-(1-hydroxyethyl)benzamide (400 mg, 2.45 mmol) slurried in DCM (20 mL) and the reaction mixture was cooled with an ice-bath. Thionyl chloride ((255 μL, 2.47 mmol) was added dropwise and the reaction was put in the refrigerator overnight. Water was added, the reaction mixture was extracted twice with DCM, washed with a 10% HCl solution, neutralized with a saturated bicarbonate solution, treated with brine, dried (MgSO$_4$), filtered and evaporated to dryness. The crude product was recrystallized from diethylether/hexane to give 335 mg (75%) of the title compound as a white solid.

$^1$H NMR (Chloroform-d) δ 7.90 (s, 1H) 7.73 (d, 1H) 7.62 (d, 1H) 7.46 (t, 1H) 5.14 (q, 1H) 1.88 (d, 3H) 1.60 (s, 2H);

MS (ESI$^+$) m/z 183, 185 [M+H]$^+$.

b) 3-{1-[(7-{[(1R)-1-(Hydroxymethyl)-3-methylbutyl]amino}-2-oxo-2,3-dihydro[1,3]thiazo[4,5-d]pyrimidin-5-yl)thio]ethyl}benzamide The title compound was obtained as a mixture of two diastereomers in 36% yield using general method G starting from 5-[7-{[(1R)-1-(hydroxymethyl)-3-methylbutyl]amino}-[1,3]thiazolo[4,5-d]pyrimidin-2(3H)-one-5-yldisulfanyl]-7-{[(1R)-1-(hydroxymethyl)-3-methylbutyl]amino}[1,3]thiazolo[4,5-d]pyrimidin-2(3H)-one (30 mg, 0.050 mmol) and 3-(1-chloro-ethyl)-benzamide (18 mg, 0.10 mmol).

The diasteromers of the title compound (58.6 mg, 0.131 mmol) were purified by reversed phase HPLC [Kromacil-C18 column, 250×20 mm, particle size=10 μm, flow=15 mL/min, mobile phase=water/MeCN/triethylamine (80/20/0.1; v/v/v)]. Lyophilization gave 3-{(1S)-1-[(7-{[(1R)-1-(Hydroxymethyl)-3-methylbutyl]amino}-2-oxo-2,3-dihydro[1,3]thiazolo[4,5-d]pyrimidin-5-yl)thio]ethyl}benzamide-(23 mg, 39% yield, 99.9% de).

¹H NMR (CD₃OD) δ 7.98 (s, 1H), 7.73 (d, 1H, J=7.7 Hz), 7.68 (d, 1H, J=7.7 Hz), 7.42 (t, 1H, J=7.6 Hz), 5.08 (q, 1H, J=7.3 Hz), 4.49-4.40 (m, 1H), 3.52 (dd, 1H, J=11.0, 5.4 Hz), 3.53 (dd, 1H, J=11.0, 5.4 Hz), 1.94 (s, 2H), 1.73 (d, 2H, J=7.2 Hz), 1.71-1.63 (m, 1H), 1.56-1.41 (m, 2H), 0.96 (d, 3H, J=7.1 Hz), 0.94 (d, 3H, J=7.1 Hz

MS (ESI) m/z 448 [M+1];

and 3-{(1R)-1-[(7-{[(1R)-1-(Hydroxymethyl)-3-methylbutyl]amino}-2-oxo-2,3-dihydro[1,3]thiazolo[4,5-d]pyrimidin-5-yl)thio]ethyl}benzamide (19 mg, 32% yield, 99.9% de).

¹H NMR (CD₃OD) δ 7.98 (s, 1H), 7.73 (d, 1H, J=7.8 Hz), 7.68 (d, 1H, J=7.8 Hz), 7.41 (t, 1H, J=7.7 Hz), 5.05 (q, 1H, J=7.3 Hz), 4.35-4.28 (m, 1H), 3.60 (dd, 1H, J=10.8, 5.8 Hz), 3.53 (dd, 1H, J=10.8, 5.8 Hz), 1.94 (s, 2H), 1.72 (d, 2H, J=7.1 Hz), 1.68-1.58 (m, 1H), 1.55-1.39 (m, 2H), 0.92 (d, 3H, J=6.7 Hz), 0.82 (d, 3H, J=6.6 Hz).

MS (ESI) m/z 448 [M+1].

EXAMPLE 15

7-{[(1R-1-(Hydroxymethyl-3-methylbutyl]amino-5-[(1-phenylpropyl)thiol][1,3]thiazolo[4,5-d]pyrimidin-2(3H)-one The title compound was obtained as a mixture of two diastereomers in 41% yield using general method G starting from 5-[7-{[(1R)-1-(hydroxymethyl)-3-methylbutyl]amino}-[1,3]thiazolo[4,5-d]pyrimidin-2(3H)-one-5-yldisulfanyl]-7-{[(1R)-1-(hydroxymethyl)-3-methylbutyl]amino}[1,3]thiazolo[4,5-d]pyrimidin-2(3H)-one (30 mg, 0.050 mmol) and (1-chloropropyl)benzene (15 mg, 0.10 mmol).

¹H NMR (DMSO-d₆) δ 12.31 (br. s., 1H), 7.45-7.28 (m, 4H), 7.28-7.14 (m, 2H), 4.77-4.65 (m, 2H), 4.40-4.19 (m, 1H), 3.51-3.31 (m, 2H), 2.16-2.02 (m, 1H), 2.02-1.86 (m, 1H), 1.69-1.54 (m, 1H), 1.52-1.32 (m, 2H), 0.95-0.76 (m, 9H);

MS (ESI) m/z 419 [M+1].

EXAMPLE 16

5-{[(1S)-1-(2-fluorophenyl)ethyl]thio}-7-{[(1R)-1-(hydroxymethyl)-3-methylbutyl]amino}[1,3]thiazolo[4,5-d]pyrimidin-2(3H)-one a) 1-[(1R)-1-Chloroethyl]-2-fluorobenzene The title compound was obtained in 65% yield with 93% enantiomeric excess using general method F starting from (1S)-1-(2-fluorophenyl)ethanol (3.56 g, 25 mmol).

¹H NMR (CDCl₃) δ 7.53 (td, 1H), 7.28 (m, 1H), 7.16 (m, 1H), 7.04 (m, 1H), 5.42 (q, 1H), 1.84 (d, 3H);
MS (ESI⁺) m/z 158 [M+H]⁺.

b) (2R)-2-[(2-Amino-5-{[(1S)-1-(2-fluorophenyl)ethyl]thio}[1,3]thiazolo[4,5-d]pyrimidin-7-yl)amino]-4-methylpentan-1-ol The title compound was obtained in 41% yield using general method A starting from (2R)-2-[(2-amino-5-mercapto[1,3]thiazolo[4,5-d]pyrimidin-7-yl)amino]-4-methylpentan-1-ol (800 mg, 2.67 mmol), and 1-[(1R)-1-chloroethyl]-2-fluorobenzene (509 mg, 3.21 mmol).

¹H NMR (DMSO-d₆) δ 7.97 (s, 2H), 7.53 (td, 1H), 7.29 (m, 1H), 7.17 (m, 1H), 7.15 (d, 1H), 6.89 (d, 1H), 5.22 (q, 1H), 4.61 (t, 1H), 4.24 (br s, 1H), 3.38 (dt, 1H), 3.28 (m, 1H), 1.65 (d, 3H), 1.59 (m, 1H), 1.49-1.32 (m, 2H), 0.87 (d, 3H), 0.84 (d, 3H);

MS (ESI⁺) m/z 422 [M+H]⁺.

c) (2R)-2-[(2-chloro-5-{[(1S)-1-(2-fluorophenyl)ethyl]thio}[1,3]thiazolo[4,5-d]pyrimidin-7-yl)amino]-4-methylpentan-1-ol The title compound was obtained in 72% yield according to general method B and starting from (2R)-2-[(2-Amino-5-{[(1S)-1-(2-fluorophenyl)ethyl]thio}[1,3]thiazolo[4,5-d]pyrimidin-7-yl)amino]-4-methylpentan-1-ol (1.12 g, 2.67 mmol).

¹H NMR (400 MHz, DMSO-d₆) δ ppm 8.08 (d, J=8.4 Hz, 1H), 7.56 (td, J=7.6, 1.6 Hz, 1H), 7.31 (m, 1H), 7.20 (m, 1H), 7.17 (d, J=7.7 Hz, 1H), 5.25 (q, J=7.0 Hz, 1H), 4.73 (t, J=5.3 Hz, 1H), 4.33 (m, 1H) 3.43-3.33 (m, 2H), 1.69 (d, J=7.0 Hz, 3H), 1.59 (m, 1H), 1.48 (m, 1H), 1.38 (m, 1H), 0.87 (d, J=6.6 Hz, 3H), 0.84 (d, J=6.6 Hz, 3H);

MS (ESI) m/z 441 [M+1].

d) (2R)-2-[(5-{[(1S)-1-(2-fluorophenyl)ethyl]thio}-2-methoxy[1,3]thiazolo[4,5-d]pyrimidin-7-ylamino]-4-methylpentan-1-ol The title compound was obtained in 85% yield using general method C (except reaction mixture was stirred at 40° C. until reaction was complete) starting from (2R)-2-[(2-chloro-5-{[(1S)-1-(2-fluorophenyl)ethyl]thio}[1,3]thiazolo[4,5-d]pyrimidin-7-yl)amino]-4-methylpentan-1-ol (200 mg, 0.45 mmol).

MS (ESI) m/z 437 [M+H]⁺.

e) 5-{[(1S)-1-(2-fluorophenyl)ethyl]thio}-{[(1R)-1-(hydroxymethyl)-3-methylbutyl]amino}[1,3]thiazolo[4,5-d]pyrimidin-2(3H)-one The title compound was obtained as a solid in 38% yield using general method D starting from (2R)-2-[(5-{[(1S)-1-(2-fluorophenyl)ethyl]thio}-2-methoxy[1,3]thiazolo[4,5-d]pyrimidin-7-yl)amino]-4-methylpentan-1-ol (140 mg, 0.32 mmol).

¹H NMR (DMSO-d₆) δ 12.36 (s, 1H) 7.55 (t, 1H) 7.24-7.35 (m, 2H) 7.16-7.22 (m, 2H) 5.20 (q, 1H) 4.65 (m, 1H) 4.28 (m, 1H) 3.37 (m, 1H) 3.29 (m, 1H) 1.68 (d, 3H) 1.60 (m, 1H) 1.47 (m, 1H) 1.37 (m, 1H) 0.87 (m, 6H);

MS (ESI⁺) m/z 423 [M+H]⁺.

EXAMPLE 17

3-{(1S)-1-[(7-{[(1R)-1-(hydroxymethyl)-3-methylbutyl]amino}-2-oxo-2,3-dihydro[1,3]thiazolo[4,5-d]pyrimidin-5-yl)thio]ethyl}benzonitrile a) 3-[(1R)-1-Chloroethyl]benzonitrile The title compound was obtained in 79% yield according to general method F starting from 3-[(1S)-1-hydroxyethyl]benzonitrile (3.35 g, 22.8 mmol).

¹H NMR (DMSO-d₆): δ 7.97 (s, 1H), 7.82 (m, 2H), 7.60 (t, 1H), 5.40 (q, 1H), 1.80 (d, 3H);

¹³C NMR (DMSO-d₆): δ 144.1, 131.2, 131.6, 130.3, 129.9, 118.4, 111.6, 57.41, 25.5;

MS (ESI⁺) m/z 166 [M+H]⁺.

b) 3-{(1S)-1-[(2-Amino-7-{[(1R)-1-(hydroxymethyl)-3-methylbutyl]amino}[1,3]thiazolo[4,5-d]pyrimidin-5-yl)thio]ethyl}benzonitrile The title compound was prepared in 31% yield from (2R)-2-[(2-amino-5-mercapto[1,3]thiazolo[4,5-d]pyrimidin-7-yl)amino]-4-methylpentan-1-ol (200 mg, 0.67 mmol) and 3-[(1R)-1-chloroethyl]benzonitrile (166 mg, 1.0 mmol) according to general method A.
$^1$H NMR (CD$_3$OD) δ 7.89-7.76 (m, 2H) 7.57 (d, 1H) 7.49 (m, 1H) 5.12 (q, 1H) 4.42 (br s, 1H) 3.53 (m, 1H) 3.44 (m, 1H) 1.63-1.76 (m, 4H) 1.41-1.60 (m, 2H) 0.96 (t, 6H);
MS (ESI$^+$) m/z 429 [M+H]$^+$.

c) 3-{(1S)-1-[(2-chloro-7-{[(1R)-1-(hydroxymethyl)-3-methylbutyl]amino}[1,3]thiazolo[4,5-d]pyrimidin-5-yl)thio]ethyl}benzonitrile The title compound was obtained as a solid in 70% yield using general method B (except upon completion the reaction mixture was poured onto ice and precipitated material was collected by filtration) starting from 3-{(1S)-1-[(2-amino-7-{[(1R)-1-(hydroxymethyl)-3-methylbutyl]amino}[1,3]thiazolo[4,5-d]pyrimidin-5-yl)thio]ethyl}benzonitrile (92 mg, 0.21 mmol).
MS (ESI$^+$) m/z 449 [M+H]$^+$.

d) 3-{(1S)-1-[(7-{[(1R)-1-(hydroxymethyl)-3-methylbutyl]-amino}-2-methoxy[1,3]triazolo[4,5-d]pyrimidin-5-yl)thio]ethyl}benzonitrile The title compound was obtained in 45% yield using general method C (except reaction mixture was stirred at 40° C. until reaction was complete) starting from 3-{(1S)-1-[(2-chloro-7-{[(1R)-1-(hydroxymethyl)-3-methylbutyl]amino}[1,3]thiazolo[4,5-d]pyrimidin-5-yl)thio]ethyl}benzonitrile (67 mg, 0.15 mmol).
MS (ESI$^+$) m/z 444 [M+H]$^+$.

e) 3-{(1S)-1-[(7-{[(1R)-1-hydroxymethyl)-3-methylbutyl]amino}-2-oxo-2,3-dihydro[1,3]thiazolo[4,5-d]pyrimidin-5-yl)thio]ethyl}benzonitrile The title compound was obtained as a solid in 32% yield using general method D starting from 3-{(1S)-1-[(7-{[(1R)-1-(hydroxymethyl)-3-methylbutyl]amino}-2-methoxy[1,3]thiazolo[4,5-d]pyrimidin-5-yl)thio]ethyl}benzonitrile (60 mg, 0.14 mmol).
$^1$H NMR (DMSO-d$_6$) δ 12.41 (s, 1H) 7.93 (s, 1H) 7.84 (d, 1H) 7.71 (d, 1H) 7.53 (t, 1H) 7.25 (d, 1H) 4.95 (q, 1H) 4.25 (m, 1H) 3.27 (m, 1H) 1.67 (d, 3H) 1.56 (m, 1H) 1.34-1.49 (m, 2H) 0.86 (m, 6H);
MS (ESI$^+$) m/z 430 [M+H]$^+$.

EXAMPLE 18

7-{[(1R)-3-fluoro-1-(hydroxymethyl)-3-methylbutyl]amino}-5-{[(1S)-1-(2-fluorophenyl)ethyl]thio}[1,3]thiazolo[4,5-d]pyrimidin-2(3H)-one a) 1-[(1R)-1-Chloroethyl]-2-fluorobenzene The title compound was obtained in 65% yield with 93% enantiomeric excess using general method F starting from (1S)-1-(2-fluorophenyl)ethanol (3.56 g, 25 mmol).
$^1$H NMR (CDCl$_3$) δ 7.53 (td, 1H), 7.28 (m, 1H), 7.16 (m, 1H), 7.04 (m, 1H), 5.42 (q, 1H), 1.84 (d, 3H);
MS (ESI$^+$) m/z 158 [M+H]$^+$.

b) 6-Amino-2-{[(1S)-1-(2-fluorophenyl)ethyl]thio}pyrimidin-4-ol

NaH (60% in oil, 1.05 g, 26.3 mmol) was added in portions followed by NaBH$_4$ (0.099 g, 2.7 mmol) to 6-amino-2-mercaptopyrimidin-4-ol monohydrate (4.23 g, 26.3 mmol) in DMF (40 mL). After 30 minutes, 1-[(1R)-1-chloroethyl]-2-fluorobenzene (5.0 g, 31.5 mmol) in DMF (10 mL) was added and the reaction mixture was stirred for 24 h. The reaction mixture was concentrated and partitioned between water and DCM, the organic phase was dried (MgSO$_4$) and evaporated. The residue was purified by flash column chromatography (a stepwise gradient of 5-10% MeOH in CHCl$_3$) to give the title compound (5.20 g, 75% yield).
$^1$H NMR (400 MHz, DMSO-d$_6$): δ 7.35 (m, 1H), 7.13 (m, 1H), 6.99 (m, 2H), 6.29 (s, 2H), 5.00 (q, 1H), 4.76 (br s, 1H), 1.49 (d, 3H);
MS (ESI$^+$) m/z 266 [M+H]$^+$.

c) 2-Amino-5-{[(1S)-1-(2-fluorophenyl)ethyl]thio}[1,3]thiazolo[4,5-d]pyrimidin-7-ol KSCN (10.76 g, 110.7 mmol) and pyridine (3.9 mL, 49.2 mmol) was added to 6-amino-2-{[(1S)-1-(2-fluorophenyl)ethyl]thio}pyrimidin-4-ol (6.53 g, 24.6 mmol) in DMF (70 mL). The mixture was cooled to 0° C. and Br$_2$ was added dropwise. After 3.5 h the reaction mixture was poured into water and the formed precipitate was collected by filtration. The solid was suspended in a mixture of DMF (75 mL) and water (15 mL) and heated to 120° C. for 8 h. The reaction mixture was poured into water and the solid was collected by filtration and dried in vacuo at 40° C. to give the title compound (6.42 g, 81% yield).
MS (ESI$^+$) m/z 323 [M+H]$^+$.

d) 7-Chloro-5-{[(1S)-(2-fluorophenyl)ethyl]thio}[1,3]thiazolo[4,5-d]pyrimidin-2-amine POCl$_3$ (2.77 mL, 29.7 mmol) was added to DMF (3.07 mL, 39.6 mmol) in dioxane (30 mL). After 30 minutes this mixture was added to a solution of 2-amino-5-{[(1S)-1-(2-fluorophenyl)ethyl]thio}[1,3]thiazolo[4,5-d]pyrimidin-7-ol (6.38 g, 19.8 mmol) in dioxane (100 mL). After 30 minutes POCl$_3$ (2.77 mL, 29.7 mmol) was added, the reaction mixture was heated to 80° C. for 2 h. After cooling to room temperature, water (20 mL) was carefully added and the resulting mixture was stirred at 80° C. for 30 minutes and at room temperature for 2 h. The reaction mixture was poured into water and the formed precipitate was collected. The solid was purified by flash column chromatography (5% MeOH in CHCl$_3$) to give the title compound (5.91 g, 88% yield).
$^1$H NMR (400 MHz, DMSO-d$_6$): δ 8.94 (s, 2H), 7.58 (m, 1H), 7.32 (m, 1H), 7.20 (m, 2H), 5.22 (q, 1H), 1.71 (d, 3H);
MS (ESI$^+$) m/z 341 [M+H]$^+$.

e) (2R)-2-[(2-Amino-5-{[(1S)-1-(2-fluorophenyl)ethyl]thio}[1,3]thiazolo[4,5-d]pyrimidin-7-yl)amino]-4-fluoro-4-methylpentan-1-ol DIPEA (2.09 mL, 12.0 mmol) was added to 7-chloro-5-{[(1S)-1-(2-fluorophenyl)ethyl]thio}[1,3]thiazolo[4,5-d]pyrimidin-2-amine (1.36 g, 4.0 mmol) and (2R)-2-amino-4-fluoro-4-methylpentan-1-ol (4 mmol) in NMP (3 mL). After stirring the reaction mixture at 120° C. for 22 h it was poured into water and the precipitate was collected by filtration. The solid was purified by flash column chromatography (a stepwise gradient of 5%-10% MeOH in CHCl$_3$) and preparative HPLC to give the title compound (0.22 g, 13% yield).

$^1$H NMR (400 MHz, CD$_3$OD): δ 7.35 (m, 1H), 7.03 (m, 1H), 6.91 (m, 2H), 5.15 (q, 1H), 4.40 (m, 1H), 3.35-3.21 (m, 2H), 1.82-1.72 (m, 2H), 1.50 (d, 3H), 1.17 (m, 6H);

MS (ESI$^+$) m/z 440 [M+H]$^+$.

f) (2R)-2-[(2-Chloro-5-{[(1S)-1-(2-fluorophenyl)ethyl]thio}[1,3]thiazolo[4,5-d]pyrimidin-7-yl)amino]-4-fluoro-4-methylpentan-1-ol The title compound was prepared using general method B starting from (2R)-2-[(2-amino-5-{[(is)-1-(2-fluorophenyl)ethyl]thio}[1,3]thiazolo[4,5-d]pyrimidin-7-yl)amino]-4-fluoro-4-methylpentan-1-ol (0.20 g, 0.44 mmol) and NaNO$_2$ (0.092 g, 1.33 mmol).

MS (ESI$^+$) m/z 459 [M+H]$^+$.

g) (2R)-4-Fluoro-2-[(5-{[(1S)-1-(2-fluorophenyl)ethyl]thio}-2-methoxy[1,3]thiazolo[4,5-d]pyrimidin-7-yl)amino]-4-methylpentan-1-ol KOH (0.050 g, 0.89 mmol) was added to (2R)-2-[(2-chloro-5-{[(1S)-1-(2-fluorophenyl)ethyl]thio}[1,3]thiazolo[4,5-d]pyrimidin-7-yl)amino]-4-fluoro-4-methylpentan-1-ol in MeOH (5 mL) and the mixture was heated to 50° C. After 3 h the mixture was diluted with NaCl (aq) and extracted with CHCl$_3$, the organic phase was dried (MgSO$_4$) and evaporated to give the title compound.

MS (ESI$^+$) m/z 455 [M+H]$^+$.

h) 7-{[(1R)-3-Fluoro-1-(hydroxymethyl)-3-methylbutyl]amino}-5-{[(1S)-1-(2-fluorophenyl)ethyl]thio}[1,3]thiazolo[4,5-d]pyrimidin-2(3H)-one Using general method D and starting from (2R)-4-fluoro-2-[(5-{[(1S)-1-(2-fluorophenyl)ethyl]thio}-2-methoxy[1,3]thiazolo[4,5-d]pyrimidin-7-yl)amino]-4-methylpentan-1-ol the title compound was obtained (0.067 g, 34% yield calculated for steps f-h).

$^1$H NMR (400 MHz, CD$_3$OD): δ 7.57 (m, 1H), 7.29 (m, 1H), 7.19-7.08 (m, 2H), 5.34 (q, 1H), 4.62 m, 1H), 3.58-3.45 (m, 2H), 2.08-1.90 (m, 2H);

MS (ESI$^+$) m/z 441 [M+H]$^+$.

EXAMPLE 19

5-{[(1S)-1-(2-fluorophenyl)ethyl]thio}-7-{[(1R)-1-(hydroxymethyl)butyl]amino}[1,3]thiazolo[4,5-d]pyrimidin-2(3H)-one a) (2R)-2-[(2-Amino-5-{[(1S)-1-(2-fluorophenyl)ethyl]thio}[1,3]thiazolo[4,5-d]pyrimidin-7-yl)amino]pentan-1-ol The title compound was obtained in 96% yield using general method A starting from (2R)-2-[(2-amino-5-mercapto[1,3]thiazolo[4,5-d]pyrimidin-7-yl)amino]pentan-1-ol (703 mg, 2.46 mmol) and 1-[(1R)-1-chloroethyl]-2-fluorobenzene (469 mg, 2.96 mmol).

$^1$H NMR (DMSO-d$_6$) δ 8.38 (br s, 2H), 7.55 (td, 1H), 7.32 (m, 1H), 7.20 (m, 1H), 7.18 (d, 1H), 5.26 (q, 1H), 4.19 (br s, 1H), 3.43 (dd, 5.6 Hz, 1H), 3.35 (dd, 1H), 1.69 (d, 3H), 1.66-1.42 (m, 2H), 1.39-1.21 (m, 2H), 0.86 (t, 3H);

MS (ESI$^+$) m/z 408 [M+H]$^+$.

b) (2R)-2-[(2-Chloro-5-{[(1S)-1-(2-fluorophenyl)ethyl]thio}[1,3]thiazolo[4,5-d]pyrimidin-7-yl)amino]pentan-1-ol The title compound was prepared using general method B starting from (2R)-2-[(2-amino-5-{[(1S)-1-(2-fluorophenyl)ethyl]thio}[1,3]thiazolo[4,5-d]pyrimidin-7-yl)amino]pentan-1-ol (0.32 g, 0.79 mmol) and NaNO$_2$ (0.16 g, 2.37 mmol).

MS (ESI$^+$) m/z 427 [M+H]$^+$.

c) (2R)-2-[(5-{[(1S)-1-(2-Fluorophenyl)ethyl]thio}-2-methoxy[1,3]thiazolo[4,5-d]pyrimidin-7-yl)amino]pentan-1-ol KOH (0.089 g, 1.58 mmol) was added to (2R)-2-[(2-chloro-5-{[(1S)-1-(2-fluorophenyl)ethyl]thio}[1,3]thiazolo[4,5-d]pyrimidin-7-yl)amino]pentan-1-ol in MeOH (10 mL) and the mixture was heated to 50° C. After 3 h the mixture was diluted with NaCl (aq) and extracted with CHCl$_3$, the organic phase was dried (MgSO$_4$) and evaporated to give the title compound.

MS (ESI$^+$) m/z 423 [M+H]$^+$.

d) 5-{[(1S)-1-(2-fluorophenyl)ethyl]thio}-7-{[(1R)-1-(hydroxymethyl)butyl]amino}[1,3]thiazolo[4,5-d]pyrimidin-2(3H)-one Using general method D and starting from (2R)-2-[(5-{[(1S)-1-(2-fluorophenyl)ethyl]thio}-2-methoxy[1,3]thiazolo[4,5-d]pyrimidin-7-yl)amino]pentan-1-ol the title compound was obtained (0.22 g, 67% yield calculated for steps b-d).

$^1$H NMR (400 MHz, CDCl$_3$): δ 7.56 (t, 1H), 7.18 (q, 1H), 7.08 (t, 1H), 7.00 (t, 1H), 5.51 (d, 1H), 5.26 (q, 1H), 4.30 8 (br s, 1H), 3.59 (m, 2H), 1.65 (d, 3H), 1.60-1.36 (m, 4H), 0.93 (t, 3H);

MS (ESI) m/z 409 [M+H]$^+$.

EXAMPLE 20

5-{[(1S)-1-(3-fluorophenyl)ethyl]thio}-7-{[(1R)-1-(hydroxymethyl)-3-methylbutyl]amino}[1,3]thiazolo[4,5-d]pyrimidin-2(3H)-one a) 1-[(1R)-1-Chloroethyl]-3-fluorobenzene

The title compound was obtained in 49% yield with 94.5% enantiomeric excess using general method F starting from (1S)-1-(3-fluorophenyl)ethanol (4.20 g, 30 mmol).

$^1$H NMR (300 MHz, DMSO-d$_6$) δ 7.47-7.30 (m, 3H); 7.16 (t, 1H); 5.36 (q, 1H); 1.78 (d, 3H).

b) (2R)-2-[(2-Amino-5-{[(1S)-1-(3-fluorophenyl)ethyl]thio}[1,3]thiazolo[4,5-d]pyrimidin-7-yl)amino]-4-methylpentan-1-ol The title compound was obtained in 61% yield using general method A starting from (2R)-2-[(2-amino-5-mercapto[1,3]thiazolo[4,5-d]pyrimidin-7-yl)amino]-4-methylpentan-1-ol (0.30 g, 1.0 mmol), 1-[(1R)-1-chloroethyl]-3-fluorobenzene (0.17 g, 1.1 mmol) and NaBH$_4$ (0.019 g, 0.5 mmol).

$^1$H NMR (400 MHz, CD$_3$OD): δ 7.23 (m, 2H), 7.13 (m, 1H), 6.86 (m, 1H), 5.01 (q, 1H), 4.38 (m, 1H), 3.43 (m, 2H), 1.63 (d, 3H), 1.44 (m, 2H), 0.88 (m, 6H);

MS (ESI$^+$) m/z 422 [M+H]$^+$.

c) (2R)-2-[(2-Chloro-5-{[(1S)-1-(3-fluorophenyl) ethyl]thio}[1,3]thiazolo[4,5-d]pyrimidin-7-yl) amino]-4-methylpentan-1-ol The title compound was prepared using general method B starting from (2R)-2-[(2-amino-5-{[(1S)-1-(3-fluorophenyl) ethyl]thio}[1,3]thiazolo[4,5-d]pyrimidin-7-yl)amino]-4-methylpentan-1-ol (0.24 g, 0.56 mmol) and $NaNO_2$ (0.12 g, 1.69 mmol).

MS (ESI$^+$) m/z 441 [M+H]$^+$.

d) (2R)-2-[(5-{[(1S)-1-(3-Fluorophenyl)ethyl]thio}-2-methoxy[1,3]thiazolo[4,5-d]pyrimidin-7-yl) amino]-4-methylpentan-1-ol KOH (0.063 g, 1.12 mmol) was added to (2R)-2-[(2-chloro-5-{[(1S)-1-(3-fluorophenyl)ethyl]thio}[1,3]thiazolo [4,5-d]pyrimidin-7-yl)amino]-4-methylpentan-1-ol in MeOH (5 mL) and the mixture was heated to 50° C. After 4 h the mixture was diluted with NaCl (aq) and extracted with $CHCl_3$, the organic phase was dried ($MgSO_4$) and evaporated to give the title compound.

MS (ESI$^+$) m/z 437 [M+H]$^+$.

e) 5-{[(1S)-1-(3-Fluorophenyl)ethyl]thio}-7-{[(1R)-1-(hydroxymethyl)-3-methylbutyl]amino}[1,3]thiazolo[4,5-d]pyrimidin-2(3H)-one Using general method D and starting from (2R)-2-[(5-{[(1S)-1-(3-fluorophenyl)ethyl]thio}-2-methoxy[1,3]thiazolo[4,5-d]pyrimidin-7-yl)amino]-4-methylpentan-1-ol the title compound was obtained (0.16 g, 65% yield calculated for steps c-e).

$^1$H NMR (400 MHz, $CD_3OD$): δ 7.30 (m, 2H), 7.19 (m, 1H), 6.95 (m, 1H), 5.02 (q, 1H), 4.44 (m, 1H), 3.49 (m, 2H), 1.69 (m, 4H), 1.55-1.40 (m, 2H), 0.94 (m, 6H);

MS (ESI$^+$) m/z 423 [M+H]$^+$.

Pharmacological Screens

Materials

Recombinant human fractalkine (hCX$_3$CL1) and recombinant human interleukin-8 (IL-8 or hCXCL8) were purchased from PeproTech Inc., UK. Recombinant [$^{125}$I]-fractalkine (human) and [$^{125}$I]hIL-8 with the specific activity of 2200 Ci/mmol, was purchased from NEN® Life Science Products, Inc., UK. Fluo-4-AM was purchased from Molecular Probes, US. All other chemicals were of analytical grade.

Cells

The complete human CX3CR1 cDNA (GenBank accession number U20350) was extracted from human brain mRNA (Superscript, Life Technologies) and ligated into pCR-Blunt II TOPO vector (InVitrogen). The insert corresponding hCX3CR1 was isolated and further subcloned into pcDNA3.1zeo. Plasmid DNA was prepared using Plasmid Midi Kit (Qiagen). Using Superfect Transfection Reagent (Qiagen) according to the manufacturer's protocol the expression plasmid for hCX$_3$CR1 was then introduced into human embryonic kidney suspension (HEKS) 293 cell line containing a vector for stable expression of a chimeric G-protein Goxqis. A stable clone was generated utilizing zeocin (500 μg/mL) and hygromycin (100 μg/mL) selection. For further applications the cells were maintained in Dulbecco's modified Eagle's medium/Ham's nutrient mix F12 (DMEM/F12) containing pyridoxine and supplemented with 10% (v/v) fetal bovine serum, 2 mM L-glutamine, 100 U/ml penicillin and 100 mg/ml streptomycin, 250 μg/mL zeocin and 100 μg/mL hygromycin.

Cells expressing human CXCR2 obtained from AstraZeneca Charnwood are cultured in EMEM containing Glutamax and supplemented with 10% FBS (from PAA, Austria), 1% non-essential amino acids (NEAA), 100 U/mL penicillin and 100 μg/mL streptomycin (PEST) and 500 μg/mL geneticin/G418.

Membrane Preparation

Cells are grown at 37° C. and 5% $CO_2$ and harvested at 60-80% confluence in buffer containing 10 mM Tris-HCl pH 7.4, 5 mM EDTA, 0.1 mg/mL bacitracin. The cells are centrifuged at 300×g for 10 min and the pellet is resuspended in harvesting buffer (10 mM Tris-HCl, pH 7.4, 5 mM ethylenediaminetetra-acetic acid (EDTA) and 0.1 mg/mL bacitracin), pooled and homogenised using a Dounce homogeniser. The homogenate is centrifuged in 48000×g for 10 min and resuspended in harvesting buffer using Ultra-Turrax T8. Membrane aliquots are stored at −80° C. Protein concentration was determined in microtiter plates as described by Harrington (1990, Anal. Biochem. 186, 285-287).

In Vitro Receptor Binding Assay

Competition binding studies of [$^{125}$I]fraktalkine were performed in 2 mL 96-deep-well plates (Beckman, Germany) in a total volume of 1000 mL/well. Each well contained 10 μM [$^{125}$I]-fractalkine and membrane equivalent to receptor concentration of 1 μM in assay buffer (50 mM Hepes-KOH, pH 7.4, 10 mM $MgCl_2$, 1 mM EDTA, 0.1% (w/v) gelatine). Ten concentrations (2 points/log unit) of the test compounds were pre-dissolved in DMSO and added to reach a final concentration of 1% (v/v) DMSO. The assay was initiated with the addition of membranes and incubated at 25° C. for 24 h. The reactions were stopped by rapid filtration through Whatman GF/B glass fiber filters pretreated with 0.3% polyethylimine and subsequent washing with ice-cold buffer (10 mM Hepes-KOH pH 7.4, 500 mM NaCl) using a Brandel receptor binding harvester. Scintillation cocktail was added and radioactivity was determined in a Packard 2500TR liquid scintillation counter. (Perkin Elmer, USA)

The [$^{125}$I]-hIL-8 competition binding studies are performed in singlicates in white clear bottom 96-well isoplates with a final volume of 200 μL and each well contains 150 pM [$^{125}$I]-hIL-8 (specific activity 2200 Ci/mmol), membrane-SPA preparation equivalent to 20 pM receptors and 1.5 mg SPA-beads in assay buffer [50 mM HEPES-KOH pH 7.4, 10 mM $MgCl_2$, 1 mM EDTA, 0.5% (w/v) gelatin]. The test compounds were treated as above. The non-specific binding is determined in the presence of 500 nM unlabelled hIL-8. The agonist hIL-8 (a concentration-response curve from 3 pM to 30 nM), is used as reference compound at each test occasion. The peptide curve does not contain DMSO. The binding reaction is started by addition of 140 μL membrane-SPA preparation, and the samples are incubated in dark at RT for 4 h. Assay plates are counted in a liquid scintillation counter (Wallac MicroBeta® TriLux 1450 from PerkinElmer, USA).

[$^{35}$S]GTPγS Binding

The [$^{35}$S]GTPγS binding studies were carried out in clear-bottom microtiter plates in duplicates with 10 concentrations of the inhibitor (2 conc/log units) diluted in DMSO (final conc 1%) and at room temperature. Membranes expressing the hCX3CR1 receptor (final concentration 20 μg protein/well) were added together with SPA beads (final concentration 1 mg/well) all suspended in GTPγS binding buffer (50 mM Tris-HCl, 100 mM NaCl, 0.1% gelatin, 15 μg saponin/mL and 3 μM GDP, pH 7.4 at rt). Membranes, SPA beads and drugs were pre-incubated 30 min before addition of 310 μM fraktalkine for maximal stimulation. Basal activity was defined as the activity found without fraktalkine stimulation (GTPγS binding buffer). After additional 30 min the reaction was started with the addition of [$^{35}$S]GTPγS to a final concentration of 0.1 nM and a final assay volume of 0.2 mL. The experiment was terminated 30 minutes later by centrifugation at 2000 rpm for 2×5 minutes (different directions) and the radioactivity determined in a liquid scintillation counter (Wallac MicroBeta® TriLux 1450).

Results

Receptor binding data for selected compounds of the present invention and for the reference compound 5-(benzylthio)-7-{[(1R)-1-(hydroxymethyl)-3-methylbutyl]amino}[1,3]thiazolo[4,5-d]pyrimidin-2(3H)-one are shown in the Table.

The reference compound 5-(benzylthio)-7-{[(1R)-1-(hydroxymethyl)-3-methylbutyl]amino}[1,3]thiazolo[4,5-d]pyrimidin-2(3H)-one was prepared from (R)-2-(5-phenylmethylthio-2-bromo-thiazolo[4,5-d]pyrimidin-7-ylamino)-4-methyl-pentan-1-ol (WO 02/076990) using general methods C and D of the present application. $^1$H NMR (400 MHz, DMSO-$d_6$) δ 12.36 (br s, 1H), 7.44-7.39 (m, 2H), 7.32-7.20 (m, 4H), 4.37-4.28 (m, 3H), 3.44-3.31 (m, 2H), 1.65-1.52 (m, 1H), 1.48-1.32 (m, 2H), 0.90-0.78 (m, 6H); LCMS (ESI$^+$) m/z 391 [M+H]$^+$.

Comparison of the data in the Table shows clearly that the compounds of the present invention wherein R$^1$ represents Me or Et are both more potent antagonists at the CX$_3$CR1 receptor and less potent antagonists at the CXCR2 receptor than the corresponding reference compound. Such enhanced selectivity with respect to antagonism of the CX$_3$CR1 receptor is expected to result in significant therapeutic benefit.

TABLE

| Compound | K$_i$ nM | |
|---|---|---|
| | CX$_3$CR1 | CXCR2 |
| Example 9 | 1.3 | 276 |
| Example 15 | 5.8 | 651 |
| Example 11 | 7.8 | 238 |
| Example 10 | 8.0 | 1359 |
| Reference Compound | 54 | 79 |

The invention claimed is:

1. A compound of formula (I)

(I)

wherein:
R$^1$ is CH$_3$ or CH$_3$CH$_2$;
R$^2$ is H, 3-CN, 2-CF$_3$, 2-F, 3-F, 3-CF$_3$, 3-CONH$_2$ or 3-SO$_2$CH$_3$;
R$^3$ is H;

R⁴ is H or CH₃; and
R⁵ is H; or, when R⁴ is CH₃, R⁵ is H or F;
or pharmaceutically acceptable salts thereof.

2. A compound according to claim 1, or pharmaceutically acceptable salts thereof, wherein R² is H, 2-F, 3-F, 3-CN or 3-SO₂CH₃.

3. A compound according to claim 1, or pharmaceutically acceptable salts thereof, wherein R⁵ is F.

4. A compound according to claim 1, or pharmaceutically acceptable salts thereof, wherein R¹ is CH₃; R² is H, 2-F or 3-CN; R³ is H; R⁴ is H or CH₃; and R⁵ is H.

5. A compound of formula (I) according to claim 1 which is:
- 7-{[(1R)-1-(hydroxymethyl)-3-methylbutyl]amino}-5-({(1R)-1-[3-(methylsulfonyl)phenyl]ethyl}thio)[1,3]thiazolo[4,5-d]pyrimidin-2(3H)-one;
- 7-{[(1R)-1-(hydroxymethyl)-3-methylbutyl]amino}-5-({1-[3-(trifluoromethyl)phenyl]ethyl}thio)[1,3]thiazolo[4,5-d]pyrimidin-2(3H)-one;
- 7-{[(1R)-1-(hydroxymethyl)butyl]amino}-5-{[(1S)-1-phenylethyl]thio}[1,3]thiazolo[4,5-d]pyrimidin-2(3H)-one;
- 7-{[(1R)-1-(hydroxymethyl)-3-methylbutyl]amino}-5-({(1S)-1-[3-(methylsulfonyl)phenyl]ethyl}thio)[1,3]thiazolo[4,5-d]pyrimidin-2(3H)-one;
- 7-{[(1R)-1-(hydroxymethyl)-3-methylbutyl]amino}-5-({1-[3-(trifluoromethyl)phenyl]ethyl}thio)[1,3]thiazolo[4,5-d]pyrimidin-2(3H)-one;
- 7-{[(1R)-1-(hydroxymethyl)-3-methylbutyl]amino}-5-({1-[2-(trifluoromethyl)phenyl]ethyl}thio)[1,3]thiazolo[4,5-d]pyrimidin-2(3H)-one;
- 7-{[(1R)-1-(hydroxymethyl)butyl]amino}-5-({(1S)-1-[3-(methylsulfonyl)phenyl]ethyl}thio)[1,3]thiazolo[4,5-d]pyrimidin-2(3H)-one;
- 7-{[(1R)-1-(hydroxymethyl)-3-methylbutyl]amino}-5-[(1-phenylethypthio][1,3]thiazolo[4,5-d]pyrimidin-2(3H)-one;
- 7-{[(1R)-1-(hydroxymethyl)-3-methylbutyl]amino}-5-{[(1R)-1-phenylethyl]thio}[1,3]thiazolo[4,5-d]pyrimidin-2(3H)-one;
- 7-{[(1R)-1-(hydroxymethyl)-3-methylbutyl]amino}-5-{[(1S)-1-phenylethyl]thio}[1,3]thiazolo[4,5-d]pyrimidin-2(3H)-one;
- 3-{(1S)-1-[(7-{[(1R)-1-(hydroxymethyl)butyl]amino}-2-oxo-2,3-dihydro[1,3]thiazolo[4,5-d]pyrimidin-5-yl)thio]ethyl}benzonitrile;
- 7-{[(1R)-1-(hydroxymethyl)-3-methylbutyl]amino}-5-({1-[3-(methylsulfonyl)phenyl]ethyl}thio)[1,3]thiazolo[4,5-d]pyrimidin-2(3H)-one;
- 3-{(1S)-1-[(7-{[(1R)-1-(Hydroxymethyl)-3-methylbutyl]amien amino}-2-oxo-2,3-dihydro[1,3]thiazolo[4,5-d]pyrimidin-5-yl)thio]ethyl}benzamide;
- 3-{(1R)-1-[(7-{[(1R)-1-(Hydroxymethyl)-3-methylbutyl]-amino}-2-oxo-2,3-dihydro[1,3]thiazolo[4,5-d]pyrimidin-5-yl)thio]ethyl}benzamide;
- 7-{[(1R-1-(hydroxymethyl)-3-methylbutyl]amino}-5-[(1-phenylpropyl)thiol][1,3]thiazolo[4,5-d]pyrimidin-2(3H)-one;
- 5-{[(1S)-1-(2-fluorophenyl)ethyl]thio}-7-{[(1R)-1-(hydroxymethyl)-3-methylbutyl]amino}[1,3]thiazolo[4,5-d]pyrimidin-2(3H)-one;
- 3-{(1S)-1-[(7-{[(1R)-1-(hydroxymethyl)-3-methylbutyl]amino}-2-oxo-2,3-dihydro[1,3]thiazolo[4,5-d]pyrimidin-5-yl)thio]ethyl}benzonitrile;
- 7-{[(1R)-3-fluoro-1-(hydroxymethyl)-3-methylbutyl]amino}-5-{[(1S)-1-(2-fluorophenyl)ethyl]thio}[1,3]thiazolo[4,5-d]pyrimidin-2(3H)-one;
- 5-{[(1S)-1-(2-fluorophenyl)ethyl]thio}-7-{[(1R)-1-(hydroxymethyl)butyl]amino}[1,3]thiazolo[4,5-d]pyrimidin-2(3H)-one;
- 5-{[(1S)-1-(3-fluorophenyl)ethyl]thio}-7-{[(1R)-1-(hydroxymethyl)-3-methylbutyl]amino}[1,3]thiazolo[4,5-d]pyrimidin-2(3H)-one;

or a pharmaceutically acceptable salt thereof.

6. A pharmaceutical formulation comprising a compound of formula (I), as defined in claim 1, or a pharmaceutically acceptable salt thereof, in admixture with a pharmaceutically acceptable diluent or carrier.

7. A pharmaceutical formulation comprising at least one compound according to claim 5, or pharmaceutically acceptable salt thereof, in admixture with a pharmaceutically acceptable diluent or carrier.

8. 7-{[(1R)-1-(hydroxymethyl)butyl]amino}-5-{[(1S)-1-phenylethyl]thio}[1,3]thiazolo[4,5-d]pyrimidin-2(3H)-one, or a pharmaceutically acceptable salt thereof.

9. A pharmaceutical formulation comprising the compound according to claim 8, or a pharmaceutically acceptable salt thereof, in admixture with a pharmaceutically acceptable diluent or carrier.

10. A method of treating cardio- and cerebrovascular atherosclerotic disorders or peripheral artery disease, which comprises administering to a person suffering from such a disease or condition, a therapeutically effective amount of a compound of formula (I), as defined in claim 1, or a pharmaceutically acceptable salt thereof.

* * * * *